United States Patent
Rasschaert et al.

(10) Patent No.: US 9,636,417 B2
(45) Date of Patent: May 2, 2017

(54) MUCOSAL MEMBRANE RECEPTOR AND USES THEREOF

(71) Applicant: Universiteit Gent, Ghent (BE)

(72) Inventors: Kristien Rasschaert, Merelbeke (BE); Bruno Goddeeris, Merelbeke (BE); Eric Cox, Merelbeke (BE); Dieter Deforce, Ghent (BE)

(73) Assignee: Universiteit Gent, Ghent (BE)

( * ) Notice: Subject to any disclaimer, the term of this patent is extended or adjusted under 35 U.S.C. 154(b) by 31 days.

(21) Appl. No.: 14/597,269

(22) Filed: Jan. 15, 2015

(65) Prior Publication Data

US 2016/0015825 A1 Jan. 21, 2016

Related U.S. Application Data

(62) Division of application No. 12/918,400, filed as application No. PCT/EP2009/001238 on Feb. 20, 2009, now Pat. No. 9,052,317.

(30) Foreign Application Priority Data

Feb. 20, 2008 (GB) .................................. 0803076.9

(51) Int. Cl.

| | |
|---|---|
| *A61K 39/395* | (2006.01) |
| *A61K 47/48* | (2006.01) |
| *G01N 33/573* | (2006.01) |
| *A61K 9/00* | (2006.01) |
| *A61K 39/002* | (2006.01) |
| *A61K 39/108* | (2006.01) |
| *A61K 39/00* | (2006.01) |

(52) U.S. Cl.
CPC ...... *A61K 47/48415* (2013.01); *A61K 9/0053* (2013.01); *A61K 39/002* (2013.01); *A61K 39/0258* (2013.01); *A61K 39/3955* (2013.01); *A61K 47/48561* (2013.01); *A61K 47/48823* (2013.01); *A61K 47/48876* (2013.01); *A61K 47/48884* (2013.01); *G01N 33/573* (2013.01); *A61K 2039/542* (2013.01); *A61K 2039/6056* (2013.01); *G01N 2333/705* (2013.01); *G01N 2333/948* (2013.01); *G01N 2500/04* (2013.01)

(58) Field of Classification Search
CPC ........ A61K 31/70; A61K 47/48; A61K 38/00; A61K 39/395; A61K 47/48415
USPC ........... 424/178.1, 184.1, 134.1, 133.1, 85.1, 424/130.1
See application file for complete search history.

(56) References Cited

U.S. PATENT DOCUMENTS

| | | | |
|---|---|---|---|
| 4,389,330 A | 6/1983 | Tice et al. | |
| 4,808,704 A | 2/1989 | Old et al. | |
| 4,818,542 A | 4/1989 | DeLuca et al. | |
| 5,137,721 A | 8/1992 | Dallas | |
| 5,348,867 A | 9/1994 | Georgiou et al. | |
| 5,698,679 A * | 12/1997 | Nemazee | C07K 14/70571 424/130.1 |
| 5,811,281 A | 9/1998 | Quaroni et al. | |
| 5,851,984 A | 12/1998 | Matthews et al. | |
| 6,007,814 A * | 12/1999 | Scheinberg | C07K 16/2896 424/130.1 |
| 6,007,996 A | 12/1999 | McNamara et al. | |
| 6,043,066 A | 3/2000 | Mangano et al. | |
| 6,066,640 A * | 5/2000 | Uckun | A61K 31/517 514/266.4 |
| 6,146,628 A * | 11/2000 | Uckun | A61K 47/48469 424/134.1 |

(Continued)

FOREIGN PATENT DOCUMENTS

| | | |
|---|---|---|
| EP | 0 367 566 A1 | 5/1990 |
| WO | 91/09955 | 7/1991 |

(Continued)

OTHER PUBLICATIONS

Erickson, A. et al.; Identification of Two Porcine Brush Border Glycoproteins That Bind the K88ac Adhesin *Escherichia coli* and Correlation of These Glycoproteins with the Adhesive Phenotype; Infection and Immunity; Mar. 1992; pp. 983-988; vol. 60, No. 3; American Society for Microbiology.
Francis, D. et al.; Expression of Mucin-Type Glycoprotein K88 Receptors Strongly Correlates with Piglet Susceptibility to K88+ Enterotoxigenic *Escherichia coli*, but Adhesion of This Bacterium to Brush Borders Does Not; Infection and Immunity; Sep. 1998; pp. 4050-4055; vol. 66, No. 9; American Society for Microbiology.
Hansen, G. et al.; The Coronavirus Transmissible Gastroenteritis Virus Causes Infection after Receptor-Mediated Endocytosis and Acid-Dependent Fusion with an Intracellular Compartment; Journal of Virology; Jan. 1998; pp. 527-534; vol. 72, No. 1; American Society for Microbiology.
Hansen, G. et al.; Cholesterol Depletion of Enterocytes; The Journal of Biological Chemistry; Feb. 18, 2000; pp. 5136-5142; vol. 275, No. 7; The American Society for Biochemistry and Molecular Biology, Inc.
Jongert, E. et al.; GRA7 provides protective immunity in cocktail DNA vaccines against Toxoplasma gondii; Parasite Immunology; 2007; pp. 445-453; vol. 29; Blackwell Publishing Ltd.

(Continued)

*Primary Examiner* — Albert Navarro
(74) *Attorney, Agent, or Firm* — Dinsmore & Shohl LLP

(57) ABSTRACT

The invention is based on the identification of aminopeptidase N (APN) as the receptor for F4 fimbriae of enterotoxigenic *E. coli* (ETEC). Based on the observation that oral administration of F4 fimbriae induces a protective intestinal mucosal immune response against a subsequent challenge with F4 ETEC, and the observation that the internalization of said F4fimbriae is clathrin-mediated, the present invention provides the characterization of APN as a target useful in: in an in vitro assay to screen for molecules that are capable to mimic the clathrin-mediated F4 endocytosis; in an in vitro assay to screen for molecules that are capable to modulate the binding of F4 fimbriae with APN; in the development of a carrier for the delivery of antigens/therapeutics, i.e. immunomodulators to the intestinal submucosa or the intestinal mucosa-associated lymphoid tissue, wherein said carrier comprises an APN specific target molecule that mimics the clathrin-mediated F4 endocytosis. The use of the carriers thus identified or the treatments thus identified, in a method of inducing an antigen specific intestinal mucosal immune response, and/or in the treatment of bacterial diarrhea, is a further aspect of the present invention.

10 Claims, 4 Drawing Sheets

(56) References Cited

U.S. PATENT DOCUMENTS

| | | | |
|---|---|---|---|
| 6,180,084 | B1 | 1/2001 | Ruoslahti et al. |
| 6,294,167 | B1 * | 9/2001 | Lindhofer ............ C07K 16/468 424/130.1 |
| 6,362,324 | B1 | 3/2002 | Kapeller-Libermann et al. |
| 6,511,662 | B1 * | 1/2003 | Zaia ..................... A61K 31/40 424/94.67 |
| 6,586,197 | B1 | 7/2003 | Adang et al. |
| 7,011,975 | B1 | 3/2006 | Adang et al. |
| 7,252,957 | B2 | 8/2007 | Vojdani |
| 8,491,894 | B2 * | 7/2013 | Lu ....................... C07K 16/2896 424/130.1 |
| 9,119,886 | B2 * | 9/2015 | Corti ................. A61K 47/48423 |
| 2001/0026937 | A1 | 10/2001 | Punnonen et al. |
| 2002/0045582 | A1 | 4/2002 | Margolin et al. |
| 2002/0131982 | A1 | 9/2002 | Morein et al. |
| 2003/0079236 | A1 | 4/2003 | Comings et al. |
| 2003/0099619 | A1 | 5/2003 | Wickham et al. |
| 2003/0119036 | A1 | 6/2003 | Chun |
| 2003/0157055 | A1 | 8/2003 | Corti |
| 2003/0157056 | A1 * | 8/2003 | Corti ..................... A61K 31/70 424/85.1 |
| 2003/0215449 | A1 | 11/2003 | Mezes et al. |
| 2004/0018171 | A1 * | 1/2004 | Corti ..................... A61K 31/70 424/85.1 |
| 2004/0096441 | A9 | 5/2004 | Ruoslahti et al. |
| 2004/0146516 | A1 * | 7/2004 | Roben ............... A61K 47/48246 424/178.1 |
| 2004/0241156 | A1 | 12/2004 | Smolyar |
| 2005/0033026 | A1 * | 2/2005 | Corti ................. A61K 47/48423 530/351 |
| 2005/0054055 | A1 | 3/2005 | Kucherlapati et al. |
| 2005/0075307 | A1 | 4/2005 | Bennett et al. |
| 2006/0024231 | A1 | 2/2006 | Schnitzer et al. |
| 2006/0024232 | A1 * | 2/2006 | Schnitzer ......... A61K 47/48561 424/1.49 |
| 2006/0073100 | A1 * | 4/2006 | Fischman ............ A61B 5/0071 424/9.6 |
| 2006/0105386 | A1 | 5/2006 | Kapeller-Libermann et al. |
| 2006/0134753 | A1 | 6/2006 | Chang et al. |
| 2006/0275763 | A1 | 12/2006 | Jorgensen et al. |
| 2007/0003522 | A1 | 1/2007 | Albritton |
| 2007/0041939 | A1 | 2/2007 | Corti |
| 2007/0072282 | A1 | 3/2007 | Chiorini et al. |
| 2007/0112050 | A1 | 5/2007 | Ashton et al. |
| 2007/0197430 | A1 * | 8/2007 | Baell ................. A61K 47/48561 514/120 |
| 2008/0026409 | A1 | 1/2008 | Danziger et al. |
| 2008/0139520 | A1 | 6/2008 | Jain et al. |
| 2008/0187487 | A1 * | 8/2008 | Larsen ................. A61K 9/5094 424/1.21 |
| 2008/0193376 | A1 * | 8/2008 | Tawakol ............ A61K 41/0057 424/1.61 |
| 2008/0305119 | A1 * | 12/2008 | Dewhurst .......... A61K 48/0058 424/178.1 |
| 2009/0110662 | A1 | 4/2009 | Breitenkamp et al. |
| 2009/0148904 | A1 | 6/2009 | Mayfield |
| 2009/0191201 | A1 * | 7/2009 | Heiss ................... A61K 31/573 424/136.1 |
| 2010/0111856 | A1 | 5/2010 | Gill et al. |
| 2010/0196458 | A1 | 8/2010 | Corti |
| 2011/0117069 | A1 | 5/2011 | Ansorge et al. |
| 2011/0305750 | A1 | 12/2011 | Beliveau et al. |
| 2012/0064624 | A1 * | 3/2012 | Lu ....................... C07K 16/2896 435/372 |
| 2012/0082728 | A1 | 4/2012 | Schneider et al. |
| 2013/0084270 | A1 | 4/2013 | Rodriguez et al. |

FOREIGN PATENT DOCUMENTS

| | | | |
|---|---|---|---|
| WO | 91/18982 | | 12/1991 |
| WO | 92/20808 | | 11/1992 |
| WO | 94/12650 | | 6/1994 |
| WO | 98/21358 | | 5/1998 |
| WO | 01/61017 | * | 8/2001 ............ C12N 15/62 |
| WO | 03/055935 | * | 10/2003 ............ C08G 69/10 |
| WO | 03/086276 | A2 | 10/2003 |
| WO | 03/092737 | * | 11/2003 ............ A61K 47/48 |
| WO | 03/092737 | A1 | 11/2003 |
| WO | 2004/041297 | * | 5/2004 ............ A61K 38/00 |
| WO | 2004/041297 | A2 | 5/2004 |
| WO | 2005/019429 | * | 3/2005 |
| WO | 2005/019429 | A2 | 3/2005 |
| WO | 2005/017977 | A2 | 12/2005 |
| WO | 2005/114207 | A2 | 12/2005 |
| WO | 2008/117999 | A2 | 12/2005 |

OTHER PUBLICATIONS

Miki, T. et al.; The Reversion-inducing Cysteine-rich Protein with Kazal Motifs (RECK) Interacts with Membrane Type 1 Matrix Metalloproteinase and CD13/Aminopeptidase N and Modulates Their Endocytic Pathways; Journal of Biological Chemistry; Apr. 20, 2007; pp. 12341-12352; vol. 282, No. 16; The American Society for Biochemistry and Molecular Biology, Inc.

Olsen, J. et al.; Complete amino acid sequence of human intestinal aminopeptidase N as deduced from cloned cDNA; Federation of European Biochemical Societies; Oct. 1988; pp. 307-314; vol. 238, No. 2; Elsevier Science Publishers.

Rasschaert, K. et al.; Screening of pigs resistant to F4 enterotoxigenic *Escherichia coli* (ETEC) infection; Veterinary Microbiology; 2007; pp. 249-253; vol. 123; Elsevier B.V.

Snoeck, V. et al.; Transcytosis of F4 fimbriae by villous and dome epithelia in F4-receptor positive pigs supports importance of receptor-dependent endocytosis in oral immunization strategies; Veterinary Immunology and Immunopathology; 2008; pp. 29-40; vol. 124; Elsevier B.V.

Van Den Broeck, W. et al.; Seroprovalence of F4+ enterotoxigenic *Escherichia coli* in regions with different pig farm densities; Veterinary Microbiology; 1999; pp. 207-216; vol. 69; Elsevier Science B.V.

Van Den Broeck, W. et al.; The F4 fimbrial antigen of *Escherichia coli* and its receptors; Veterinary Microbiology; 2000; pp. 223-244; vol. 71; Elsevier Science B.V.

Van Der Stede, Y. et al.; Antigen dose modulates the immunoglobulin isotype responses of pigs against intramuscularly administered F4-fimbriae; Veterinary Immunology and Immunopathology; 2002; pp. 209-216; vol. 88; Elsevier Science B.V.

Verdonck, F. et al.; Cholera toxin improves the F4(K88)-specific immune response following oral immunization of pigs with recombinant FaeG; Veterinary Immunology and Immunopathology; 2005; pp. 21-29; vol. 103; Elsevier B.V.

Verdonck, F. et al.; Fimbriae of enterotoxigenic *Escherichia coli* function as a mucosal carrier for a coupled heterologous antigen; Journal of Controlled Release; 2005; pp. 243-258; vol. 104; Elsevier B.V.

International Search Report dated Aug. 27, 2009 pertaining to PCT/EP2009/001238.

Li, L, et al. Generation of High Titre Antibodies to Pokeweek Antiviral Protein (PAP) in Rabbits Using Synthetic Peptides and their Use in Detection PAP in Transgenic Petunia and Yeast, Journal of Phytopathology, vol. 160, pp. 599-602, 2012.

Abnova, p. 1, downloaded Oct. 9, 2014, ANPEP Monoclonal Antibody, Clone WM15.

Pasqualini, et al., Aminopeptidase N Is a Receptor for Tumor-Homing Peptides and a Target for Inhibiting Angiogenesis, Cancer Research 2000, vol. 60, pp. 722-727.

Li, B.X., et al., Porcine Aminopeptidase N. is a Functional Receptor for the PEDV Coronavirus, Virology, vol. 365, pp. 166-172, 2007.

Ibiza-Palacios, et al., Selective Inhibition of Binding of Bacillus Thuringiensis Cry1Ab Toxin to Cadherin-Like and Aminopeptidase Proteins in Brush-Border Membranes and Dissociated Epithelial Cells from Bombyx Mori, Biochemistry Journal, Jan. 2008, vol. 409, pp. 215-221.

Bakker, et al., Abstract Only, K88 Fimbriae As Carriers of Heterologous Antigenic Determinants, vol. 8(5), May 1990, pp. 343-352.

(56) References Cited

OTHER PUBLICATIONS

Tiels, et al., The Excretion of F18+ *E.coli* is Reduced After Oral Immunization of Pigs with a FedF and F4 Fimbriae Conjugate, Vaccine, Apr. 2008, vol. 26, pp. 2154-2163.

Thiry, et al., Cloning of DNA Sequences Encoding Foreign Peptides and Their Expression in the K88 Pili, Applied and Environmental Microbiology, vol. 55, Issue 4, 1989, pp. 984-993.

Yeager, et al., Human Aminopeptidase N Is a Receptor for Human Coronavirus 229E, Nature, vol. 357, Jun. 4, 1992, pp. 420-422.

Nigatu, et al., Detection of Measles Specific IgG in Oral Fluid Using an FITC/Anti-FITC IgG Capture Enzyme Linked Immunosorbent Assay (GACELISA ), Journal of Virological Methods, vol. 83, 1999, pp. 135-144.

Tai, et al., Journal of Biological Chemistry, vol. 262, Issue 4, May 15, 1987, pp. 6803-6804.

Van Zijderveld, et al., Epitope Analysis of the F4 (K88) Fimbrial Antigen Complext of Enterotoxigenic *Escherichia coli* by Monoclonal Antibodies, Infection and Immunity, vol. 58, Issue 6, pp. 1870-1878, Jun. 1990.

Kramer, et al., Aminopeptidase N. (CD13) Is a Molecular Target of the Cholesterol Absoption Inhibitor Ezetimibe in the Enterocyte Brush Border Membrane, The Journal of Biological Chemistry, vol. 280, Issue 2, Jan. 14, 2005, pp. 1306-1320.

Verdonck, et al., The Polymeric Stabiliy of the *Escherichia coli* F4 (K88) Fimbriae Enhances Its Mucosal Immunogenicity Following Oral Immunization, Vaccine, Oct. 23, 2008, vol. 26, Issue 45, pp. 5728-5735.

Melkebeek, et al., Targeting Aminopeptidase N, A Newly Identified Recpetor for F4ac Fimbriae, Enhances the Intestinal Mucosal Immune Response Abstract Only, Mucosal Immunology, 2012, vol. 5, Issue 6, pp. 6345-6645.

Sanchez, Analysis of Filvirus Entry Into Vero E6 Cells, Using Inhiibitors of Endocytosis, Endosomal Acidifcation, Structural Integrity and Cathepsin (B and L) Actity, ournal of Infectious Disease, vol. 196, (Suppl 2), 2007, pp. S251-S258.

Bank, et al. Triggering Endogenous Immunosuppressive Mechanisms by Combined Targeting of Dipeptidyl Peptidase IV and Aminopeptidase N-A Novel Approach for Treatment of Inflammatory Bowel Disease, International Immunopharmacology, vol. 6, 2006, pp. 1925-1934.

Myers, et al., Immunotoxins for Ex Vivo Marrow Purging in Autologous Bone Marrow Transplantation for Acute Nonlymphocytic Leukemia, Transplantation, vol. 46, No. 2, pp. 240-245, Aug. 1988.

European Application No. 09 712 022.4 Office Action dated Apr. 5, 2012.

European Application No. 09 712 022.4 Office Action dated Sep. 21, 2011.

* cited by examiner

MUCOSAL MEMBRANE RECEPTOR AND USES THEREOF

CROSS REFERENCE TO RELATED APPLICATIONS

This application is a divisional of U.S. patent application Ser. No. 12/918,400 filed Nov. 10, 2010, entitled MUCOSAL MEMBRANE RECEPTOR AND USES THEREOF, which is the national stage of International PCT/EP2009/001238 filed Feb. 20, 2009, which claims the benefit of Great Britain Application No. 0803076.9 filed Feb. 20, 2008, the disclosures of which are incorporated herein by reference.

BACKGROUND OF THE INVENTION

The invention is based on the identification of aminopeptidase N (APN) as the receptor for F4 fimbriae of enterotoxigenic *E. coli* (ETEC). ETEC is an important cause of bacterial diarrheal illness. It is the leading cause of travelers' diarrhea and a major cause of diarrheal disease in underdeveloped nations. Based on the observation that oral administration of F4 fimbriae induces a protective intestinal mucosal immune response against a subsequent challenge with F4 ETEC, and the observation that the mechanism of F4 fimbriae endocytosis is clathrin-mediated, the present invention provides the characterization of APN as a target:

In an in vitro assay to screen for molecules that are capable to mimic the clathrin-mediated F4 endocytosis;

In an in vitro assay to screen for molecules that are capable to modulate the binding of F4 fimbriae with APN;

In the development of a carrier for the delivery of antigens/therapeutics, i.e. immunomodulators to the intestinal submucosa or the intestinal mucosa-associated lymphoid tissue, wherein said carrier comprises an APN specific target molecule that mimics the clathrin-mediated F4 endocytosis.

The use of the carriers thus identified or the treatments thus identified, in a method of inducing an antigen-specific intestinal mucosal immune response, and/or in the treatment of bacterial diarrhea, is a further aspect of the present invention. Enterotoxigenic *Escherichia coli*, or ETEC, is an important cause of bacterial diarrheal illness in man and animal. Infection with ETEC is the leading cause of travelers' diarrhea and a major cause of diarrheal disease in underdeveloped nations, where it can be life-threatening among children (Ratchtrachenchai 2004). In pigs, ETEC can express five types of fimbriae; F4, F5, F6, F18 and F41 of which F4 is the most frequent (80%) and is involved in diarrhea and mortality (39%) in neonatal, suckling and newly weaned piglets (Conzelman 2000).

Susceptibility to F4 *E. coli* adhesion is dominantly inherited in the host and conferred by specific receptors on the brush border of enterocytes in the small intestine (F4 receptor positive). In homozygous resistant pigs (F4 receptor negative), no adhesion of F4 fimbriae is observed. Three antigenic variants have been identified namely F4ab, F4ac and F4ad of which F4ac is by far the most common type. Interestingly, oral immunization with soluble F4ac fimbriae has been reported to result in a protective immune response against a challenge with F4ac ETEC (Van den Broeck 1999). In addition, oral administration of recombinant F4ac on itself is also able to induce an immune response and experiments using F4ac coupled to human serum albumin have demonstrated that F4ac has potential to serve as a carrier molecule to induce mucosal immune responses against coupled antigens (Verdonck 2005). We found that orally administered F4ac is endocytosed by villous enterocytes, follicle-associated enterocytes and M cells in the epithelial brush border, whereafter transcytosis occurred into the lamina propria and dome regions of the jejunal and ileal Peyer's patches (Snoeck 2008). Subsequent uptake and presentation of F4ac by antigen presenting cells could explain its capacity to induce a mucosal immune response (Snoeck 2008). This implies that targeting selected antigens to one or more of the F4ac receptors may have potential to elicit efficient mucosal immune responses against these antigens. Intestinal mucin-type glycoprotein 1 and 2 have been identified as receptors for F4ac (Francis 1998, Erickson 1992), but these have not been reported to initiate transcytosis or to induce an efficient immune response, and are therefore not likely to represent the F4ac receptors that are involved in transcytosis and mucosal immune responses.

It has thus been an object of the present invention to identify the F4ac receptor involved in triggering the observed intestinal mucosal immune response mentioned hereinbefore. The identification of this receptor and the mechanism of F4 endocytosis provides the possibility of targeting said receptor and the F4 endocytosis mechanism in the development of a carrier for delivering an agent across the mucosal barrier.

BRIEF SUMMARY OF THE INVENTION

It is accordingly, a first objective of the present invention to provide a method of delivering a compound across the mucosal barrier of a subject; said method comprising administering to said subject a compound comprising an APN specific target molecule.

The APN specific target molecule as used herein, generally refers to a molecule that selectively binds to an APN receptor and mimics the clathrin-mediated endocytosis of APN in response to *E. coli* fimbriae, and that can be identified using the APN based screening assays as provided hereinafter.

Briefly, assays to identify compounds capable of crossing the mucosal barrier and useful in the aforementioned method as APN selective target molecules, include;

- Functional assays, comprising: a) incubating a source containing an APN receptor with the compound to be tested; and b) determine the capability of said compound to bind to and induce clathrin-mediated transcytosis of said APN receptor. The capability of said compound to bind to and to induce clathrin-mediated transcytosis of said APN receptor, is typically determined by comparison to the *E. coli* fimbriae induced transcytosis of the APN receptor, in particular F4ac or F4ab.
- Binding assays, comprising a) incubating a source containing an APN receptor or a functional fragment thereof, with i) *E coli* fimbriae ii) said test compound; and b) measuring the effect of the test compound on the amount of *E. coli* fimbriae bound to the receptor. Alternatively the binding assays comprise the use of APN specific antibodies or fragments thereof, instead of *E coli* fimbriae.

Given the observation that the ETEC induced mucosal immune response is mediated via the APN receptor, it is also an object of the present invention to provide a method to identify compounds useful in conditions associated with a mucosal immune response, in particular an intestinal mucosal immune response said method comprising;

contacting aminopeptidase N (APN) expressing cells with F4 fimbriae in the presence and absence of the compound to be tested; and determine whether said compound has an effect on the interaction of APN with the F4 fimbriae, or is capable of mimicking the clathrin-mediated transcytosis of F4 fimbriae by said APN expressing cells.

APN expressing cells as used in the methods of the present invention include; primary cells isolated from small intestinal epithelial tissue, such as for example enterocyte preparations; or continuous cells including recombinant cell lines expressing APN. In a particular embodiment, the APN expressing cells are enterocyte preparations of small intestinal epithelial cells from a mammal, including, pig, human, rat, mouse, dog, cat, bovine, horse or sheep; more in particular enterocyte preparations of small intestinal cells of the pig. Alternatively, the APN expressing cells are selected from continuous intestinal epithelial cell lines selected from the group consisting of IPEC-J2 cells, BHK-21 cells, PIE cells (M. Mone et al., 2008, BBA 1780; 134-144) and CaCo2 cells.

In a further embodiment, the APN expressing cells are continuous cell lines and related cell lines (adapted from, derived from, transformed, transfected, subcloned . . . ) and any cell line transfected with APN or porcine APN; selected from the group consisting of; 12MBr6, African green monkey bronchial epithelial cells, human embryonic kidney cell line (HEK)-293, 293T/17, human kidney cell line, 2CSF-MEo, human CF lung submucosal epithelium cells, 3LL, murine Lewis lung carcinoma cells, 4MBr-5, rhesus monkey lung bronchus cells, 56FHTE8o, human fetal trachea epithelium cells, 6CSFMEo, human CF lung submucosal epithelium cells, 9HTEo-, human fetal broncho epithelium cells, A549, human lung carcinoma cells, type II pneumocytes, AK-D, cat lung cells, A-72, canine fibroblast cell line, Bing [CAK 8; CAK8], human kidney cells, BHK, baby hamster kidney cells, CaCo2, human colon carcinoma epithelial cells, Ca Ski, human cervix epidermoid carcinoma cells, CFNPE90-CF, nasal epithelium cells, CFPEo, human trachea epithelium cells, CFSMEo, human CF lung submucosal epithelium cells, CHO, hamster ovary cells, CHO-K1, subclone of hamster ovary cells, COLO 205, human colon carcinoma epithelial cells, CrFK, Crandell feline kidney cell line*, CuFi-1, lung bronchus epithelial cell line, DHD Pro.b, rat colon carcinoma cells, DLD-1, human colorectal carcinoma cell line, DoCl1 (S+L−), dog kidney cell line, EPEC, porcine intestinal epithelial cell line*, FHs 74 Int, human small intestinal cell line, FL, HeLa contaminant, FKCU, Feline kidney Colorado University (FKCU) cells, Fcwf-4, cat macrophage cell line, *Felis catus* whole foetus cells*, GPC-16, *Cavia porcellus* colorectal carcinoma cell line, H69AR, human lung cells, HaK, hamster kidney cells, HCT-15, human colon adenocarcinoma line, HCT-116, colorectal carcinoma cell line, HEK 293, human embrionic kidney cell line, HeLa, human cervix epitheloid carcinoma cells, HeLa 229, human cervix epitheloid carcinoma cells, HeLa S3, human cervix epitheloid carcinoma cells, HeLa NR1, human cervix epitheloid carcinoma cells, HEp-2, derived via HeLa contamination, HL-60, HL-60R, human myelogenous leukemia cells, HKB-11, human kidney lymphoma cell line, HRT-18G, human rectal cell line (bovine coronavirus sensitive), HT-29, human colon adenocarcinoma line, IPEC-J2, porcine intestinal epithelial cell line*, IPEC-I, porcine intestinal epithelial cell line*, IEC-18, rat ileal epithelial cell line, IEC-6, rat intestinal epithelial cell line, intestine 407, HeLa contaminant, Kasumi-3, human lymphoblast*, Kasumi-4, human myeloblast*, Kasumi-6, human myeloblast*, KU812, human basophil cell line*, L2, rat lung cell line, L-132, HeLa cell contamination*, LA-4, mouse lung adenoma cells, LLC-PK1, porcine kidney cells, LLC-MK2, rhesus monkey kidney cells, LoVo, human colon carcinoma epithelial cells, LS123, human colorectal adenocarcinoma cell line, LS 174T, human colorectal adenocarcinoma cell line, MDCK, canine kidney epithelial cells, MDBK, bovine kidney epithelial cells, MIAPaCa-2, human pancreatic cells, MLE-12, Murine lung epithelial cells, MLE-15, Murine lung epithelial cells, MRC-5, human fetal lung epithelium cells, NCI-H716, NCI-H747, NCI-H508, NCI-H498, human colorectal adenocarcinoma cell line, NCI-H2126, human lung adenocarcinoma cell line, NCI-H1688, human lung carcinoma cell line, NRK-52E, rat kidney cells, NuLi-1, human bronchus epithelial cell line, OMK(637-69), Owl monkey kidney cells, PK(15), porcine kidney cell line, RKO, human colorectal carcinoma cell line, RK13, rabbit kidney cell line, RPMI 2650, human nasal cell line, RL-65, rat lung cells, SJPL, Porcine lung epithelial cell line designated St. Jude porcine lung cells, SK-RST, Porcine kidney cortex cells*, SNU-C2B, human colorectal carcinoma cell line, ST, swine testis cell line*, SUP-B15, human B lymphoblast*, SW48, human colorectal carcinoma cell line, SW403, SW480, SW620, SW837, SW948, SW1116, SW1417, SW1463, human colorectal carcinoma cell lines, T84, human colorectal carcinoma cell line, TCMK-1, mouse kidney cell line, VERO 76, African green monkey kidney cells, WT 9-7, human epithelial kidney cortex cells*, WT 9-12, human epithelial kidney cortex cells*, W162, African green monkey kidney cells, WiDr, colon adenocarcinoma line, and WISH, HeLa cell contamination. (*aminopeptidase expressing cell line)

The conditions associated with an intestinal mucosal immune response include all kind of infections of the gastrointestinal tract (parasitic, viral, bacterial, mycotic, yeast infections), food allergies, Crohn's disease and Inflammatory and Irratable Bowel disease and IgA deficiencies. In particular said condition consists of diarrhoea, more in particular bacterial diarrhoea.

When looking for APN specific target molecules, it is to be expected that said compounds will have an effect on the interaction of APN with the F4 fimbriae, said compounds preferably compete with the interaction of APN with F4 fimbriae, but should mimic the F4 fimbriae induced endocytosis of the APN receptor. Such compounds include, but are not limited to antigens, antibodies or fragments thereof, peptides, proteins, lipids, organic molecules and nucleic acid oligomers.

In one embodiment of the present invention said compound is an APN specific antibody or an antigen-binding fragment thereof. In a further embodiment said compound is a chimeric molecule comprising an APN specific target molecule, such as an antibody or an antigen-binding fragment thereof. In such a chimeric molecule, the APN specific target molecule, e.g. APN specific antibody or an antigen-binding fragment thereof, functions as a carrier for the delivery of antigens/therapeutics, i.e. immunomodulators to the intestinal submucosa or the intestinal mucosa-associated lymphoid tissue.

Hence, in one objective of the present invention the chimeric molecule comprises an APN specific target molecule, for example an APN specific antibody or an antigen-binding fragment thereof, and a heterologous antigen, i.e. an antigen to be tested for its usefulness in conditions associated with an intestinal mucosal immune response; in particular for its usefulness as an antigen capable of inducing an antigen specific intestinal mucosal immune response; more in particular for its usefulness in oral immunization.

Heterologous antigens to be tested in the methods of the present invention include, but are not limited to proteins, lipids, nucleic acids, glycolipids and glycoproteins, carbohydrates, oligosaccharides, and polysaccharides. These include parts (coats, capsules, cell walls, flagella, fimbriae, and toxins) of bacteria, viruses and other microorganisms, wherein the lipids and nucleic acid molecules are antigenic as part of the chimeric molecule.

In another objective, the chimeric molecule, comprises an APN specific target molecule coupled with antigens or therapeutic molecules useful in the treatment/prevention of conditions associated with an intestinal mucosal immune response.

The APN specific target molecule not only includes an APN specific antibody or an antigen-binding fragment thereof, but also small molecules, organic or inorganic molecules, known to selectively bind the APN receptor, e.g. ezetimibe. Optionally the APN-specific target molecule is coupled (bound to, linked, associated or conjugated) with a particle of variable dimension and known as a microsphere, microparticle, nanoparticle, nanosphere or liposomes (e.g. superparamagnetic iron oxide nanoparticles) loaded with a therapeutic molecule.

The therapeutic molecule or compounds as used herein, refers generally to an organic or inorganic assembly of atoms of any size, and includes small molecules (less than about 2500 Daltons) or larger molecules, e.g. peptides, polypeptides, whole proteins and polynucleotides, known to have a beneficial effect in conditions associated with a mucosal immune response, in particular an intestinal mucosal immune response e.g. an anti-diarrhoea compound or an anti-inflammatory compound.

DETAILED DESCRIPTION OF THE INVENTION

Figure 1:
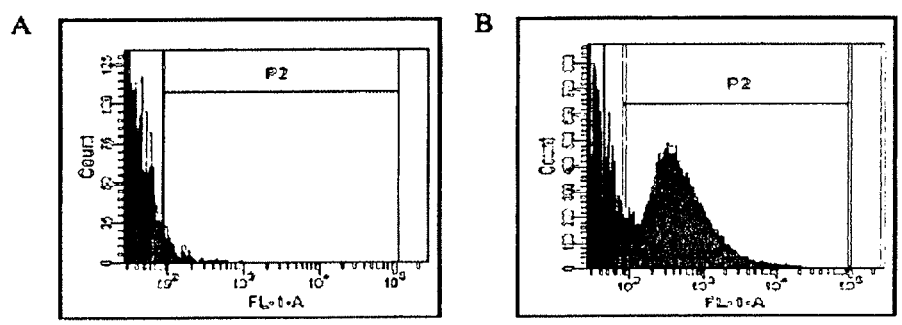
FIG. 1 FLUOS-labeled-F4 binding to pAPN transfected BHK-21 cells. Flowcytometric histogram showing fluorescence intensity of BHK-21 (A) and pAPN transfected BHK-21 cells (B).

As already mentioned hereinbefore, the present invention is based on the observation that the glycolisated aminopeptidase N (APN) is a receptor for fimbriae of enterotoxigenic *E. coli* (ETEC), in particular with the F4 fimbriae of ETEC. Binding is occurring to one of the sugars on APN. Indeed two hours treatment with periodate abolished the F4ac binding to the Brush Border Membrane Vesicles (BBMV) of F4R$^+$ pigs. Also the treatment of BBMV with a recombinant neuraminidase from *Arthobacter urefaciens*, which removes α2-3,6,8,9 linked sialic acid, resulted in a reduction in reactivity of F4 to the BBMV of F4R$^+$ pigs. This result shows that sialic acids on BBMV are involved in the binding of F4. Further investigation with glycosidases demonstrated that the sialic acids are present on the complex N-linked glycans since N-glycosidase F treatment of BBMV strongly reduced F4 binding.

The *E. coli* fimbriae—APN interaction is further characterized in that it induces a clathrin-mediated endocytosis of the APN receptor in the BBMV. This in contrast to the APN internalization of envelop viruses like infectious bronchitis virus (IBV) or (TGEV) through membrane fusion. Using this functional characterization of the *E. coli* fimbriae—APN interaction it is now possible to find and design APN specific target molecules that will mimic the *E. coli* fimbriae induced and clathrin-mediated endocytosis of the APN receptor, and that are useful in delivering an agent across the mucosal barrier.

"F4 fimbriae" are F4 or K88 fimbriae are long filamentous polymeric surface proteins of enterotoxigenic *Escherichia coli* (ETEC), consisting of so-called major (FaeG) and minor (FaeF, FaeH, FaeC, and probably FaeI) subunits. The F4 fimbriae allow the microorganisms to adhere to F4-specific receptors present on brush borders of villous enterocytes and consequently to colonize the small intestine. Such ETEC infections are responsible for diarrhea and mortality in neonatal and recently weaned pigs.

Three antigenic variants have been identified namely F4ab, F4ac and F4ad of which F4ac is the most common type. As used herein, "F4 fimbriae" is meant to include the aforementioned antigenic variants, as well as homologues of the *E. coli* F4 fimbriae, i.e. 70%, 75%, 80%, 85%, 87%, 89%, 90%, 92%, 93%, 94%, 95%, 96%, 97%, 98%, or 99% identical to any one of the aforementioned antigenic variants. In a particular embodiment, the fimbriae used in the methods of the present invention consist of the *E. coli* F4 fimbriae; more in particular *E. coli* F4ac. Said fimbriae can for example be obtained from a bacterial suspension using the methods provided in the examples hereinafter.

"aminopeptidase N (APN)" is a type II membrane glycoprotein, belongs to the family of membrane-bound metalloproteases (Olsen 1988) and is expressed in a variety of tissues among which the porcine intestinal brush border membranes. cDNA sequences that encodes a porcine APN (pAPN) polypeptide (SwiwwProt accession number P15145), a murine APN polypeptide (SwissProt access number P15684) a feline APN polypeptide (SwissProt access number P79171) a donkey APN polypeptide (Genbank access number ABR22999), a chicken APN polypeptide (UniProt/TrEMBL access number O57579), as a human variant (Genbank access number P15144), have been reported.

As used herein the "APN" polypeptide is meant to be a protein encoded by a mammalian APN gene, including allelic variants as well as biologically active fragments thereof containing conservative or non-conservative changes as well as artificial proteins that are substantially identical, i.e. 70%, 75%, 80%, 85%, 87%, 89%, 90%, 92%, 93%, 94%, 95%, 96%, 97%, 98%, or 99% identical to any one of the aforementioned APN polypeptides. In a particular embodiment the APN polypeptide is 70%, 75%, 80%, 85%, 87%, 89%, 90%, 92%, 93%, 94%, 95%, 96%, 97%, 98%, or 99% identical to the porcine APN (supra). In a further embodiment, the APN polypeptides as defined herein, are further characterized in that they are glycosilated, i.e. comprise α2-3,6,8,9 linked sialic acids.

By analogy, the "APN" polynucleotide is meant to include allelic variants as well as biologically active fragments thereof containing conservative or non-conservative changes as well as any nucleic acid molecule that is substantially identical, i.e. 70%, 75%, 80%, 85%, 87%, 89%, 90%, 92%, 93%, 94%, 95%, 96%, 97%, 98%, or 99% identical to any one of the aforementioned APN encoding polynucleotides.

cDNA sequences that encodes a porcine APN (pAPN) polypeptide (Genbank accession number NM_214277), a murine APN polypeptide (Genbank access number BC005431, BC017011, U77083) a feline APN polypeptide (Genbank accession number U58920) a donkey APN polypeptide (Genbank accession number EF442070), a chicken APN polypeptide (Genbank accession number NM_204861), as well as a human variant (Genbank accession number NM_001150, BC058928) are available.

In a particular embodiment the APN polynucleotide is 70%, 75%, 80%, 85%, 87%, 89%, 90%, 92%, 93%, 94%, 95%, 96%, 97%, 98%, or 99% identical to the nucleic acid molecule encoding for porcine APN (Genbank Acession No NM_214277).

Biologically active fragments of APN are meant to include fragments that retain the activity of the full-length protein, such as the soluble form of APN. In a particular embodiment of the present invention the functional fragments comprise the α2-3,6,8,9 linked sialic acids found on APN.

As used herein, the terms "polynucleotide" and "nucleic acid" are used interchangeably to refer polynucleotides of any length, either deoxyribonucleotides or ribonucleotides or analogs (e.g., inosine, 7-deazaguanosine, etc.) thereof. "Oligonucleotides" refer to polynucleotides of less than 100 nucleotides in length, preferably less than 50 nucleotides in length, and most preferably about 10-30 nucleotides in length. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can include modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

"Polypeptide" refers to any peptide or protein comprising amino acids joined to each other by peptide bonds or modified peptide bonds. "Polypeptide" refers to both short chains, commonly referred to as peptides, oligopeptides or oligomers, and to longer chains, generally referred to as proteins. Polypeptides may contain amino acids other than the 20 gene-encoded amino acids.

"Polypeptides" include amino acid sequences modified either by natural processes, such as post-translational processing, or by chemical modification techniques which are well known in the art. Such modifications are well described in basic texts and in more detailed monographs, as well as in a voluminous research literature.

Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications (see, for instance, Proteins-Structure and Molecular Properties, 2nd Ed., T. E. Creighton, W. H. Freeman and Company, New York, 1993; Wold, F., Post-translational Protein Modifications: Perspectives and Prospects, pgs. 1-12 in Postranslational Covalent Modification of Proteins, B. C. Johnson, Ed., Academic Press, New York, 1983; Seifter et al., "Analysis for protein modifications and nonprotein cofactors", Meth Enzymol (1990) 182: 626-646 and Rattan et al., "Protein Synthesis: Post-translational Modifications and Aging", Ann NY Acad Sci (1992) 663: 4842).

Sequence Identity

The percentage identity of nucleic acid and polypeptide sequences can be calculated using commercially available algorithms which compare a reference sequence with a query sequence. The following programs (provided by the National Center for Biotechnology Information) may be used to determine homologies/identities: BLAST, gapped BLAST, BLASTN and PSI-BLAST, which may be used with default parameters.

The algorithm GAP (Genetics Computer Group, Madison, Wis.) uses the Needleman and Wunsch algorithm to align two complete sequences that maximizes the number of matches and minimizes the number of gaps. Generally, the default parameters are used, with a gap creation penalty=12 and gap extension penalty=4.

Another method for determining the best overall match between a nucleic acid sequence or a portion thereof, and a query sequence is the use of the FASTDB computer program based on the algorithm of Brutlag et al (Comp. App. Biosci., 6; 237-245 (1990)). The program provides a global sequence alignment. The result of said global sequence alignment is in percent identity. Suitable parameters used in a FASTDB search of a DNA sequence to calculate percent identity are: Matrix=Unitary, k-tuple=4, Mismatch penalty=1, Joining Penalty=30, Randomization Group Length=0, Cutoff Score=1, Gap Penalty=5, Gap Size Penalty=0.05, and Window Size=500 or query sequence length in nucleotide bases, whichever is shorter. Suitable parameters to calculate percent identity and similarity of an amino acid alignment are: Matrix=PAM 150, k-tuple=2, Mismatch Penalty=1, Joining Penalty=20, Randomization Group Length=0, Cutoff Score=1, Gap Penalty=5, Gap Size Penalty=0.05, and Window Size=500 or query sequence length in nucleotide bases, whichever is shorter.

APN Expression

In the methods of the present invention, APN expressing cells are used. The "expression" generally refers to the process by which polynucleotides are transcribed into mRNA and/or the process by which the mRNA is subsequently translated into peptides, polypeptides or proteins.

APN expression may be facilitated or increased by methods that involve the introduction of exogenous nucleic acid into the cell. Such a cell may comprise a polynucleotide or vector in a manner that permits expression of an encoded APN polypeptide.

Polynucleotides that encode APN may be introduced into the host cell as part of a circular plasmid, or as linear DNA comprising an isolated protein-coding region, or in a viral vector. Methods for introducing exogenous nucleic acid into the host cell well known and routinely practiced in the art include transformation, transfection, electroporation, nuclear injection, or fusion with carriers such as liposomes, micelles, ghost cells, and protoplasts. Host cell systems of the invention include plant, invertebrate and vertebrate cells systems.

Hosts may include, but are not limited to, the following: insect cells, porcine kidney (PK) cells, porcine kidney cortex (SK-RST) cells porcine intestinal (IPEC-J2, IPEC-I, EPEC) cells, feline kidney (FK) cells, *felis catus* whole foetus cells (Fcwf-4), swine testicular (ST) cells, African green monkey kidney cells (MA-104, MARC-145, VERO, and COS cells), Chinese hamster ovary (CHO) cells, baby hamster kidney (BHK) cells, human 293 cells, and murine 3T3 fibroblasts, human colon carcinoma epithelial (CaCo2) cells, human lymphoblast (Kasumi-3), human myeloblast (Kasumi-4), human myeloblast (Kasumi-6), human basophil cell line (KU812), human B lymphoblast (SUP-B15), human epithelial kidney cortex cells (WT 9-7, WT 9-12). Insect host cell culture systems may also be used for the expression of the polypeptides according to the invention.

In another embodiment, the polypeptides are expressed using a *drosophila* expression system. Alternatively the polypeptides are expressed using plant-based production platforms such as for example described in Twyman R. M. et al., Molecular farming in plants: host systems and expression technology *Trends Biotechnol.* 21, 570-578.

The choice of a suitable expression vector for expression of the polypeptides according to the invention will of course depend upon the specific host cell to be used, and is within the skill of the ordinary artisan. Examples of suitable expression vectors include pSport and pcDNA3 (Invitrogen), pCMV-Script (Stratagene), and pSVL (Pharmacia Biotech). Expression vectors for use in mammalian host cells may include transcriptional and translational control sequences derived from viral genomes. Commonly used promoter sequences and modifier sequences which may be used in the present invention include, but are not limited to, those derived from human cytomegalovirus (CMV), Rous sarcoma virus (RSV), Adenovirus 2, Polyoma virus, and Simian virus 40 (SV40). Methods for the construction of mammalian expression vectors are disclosed, for example, in Okayama and Berg (Mol. Cell. Biol. 3:280 (1983)); Cosman et al. (Mol. Immunol. 23:935 (1986)); Cosman et al. (Nature 312:768 (1984)); EP-A-0367566; and WO 91/18982.

Because APN sequences are known to exist in cells from various species, the endogenous gene may be modified to permit, or increase, expression of the APN polypeptide. Cells can be modified (e.g., by homologous recombination) to provide increased expression by replacing, in whole or in part, the naturally occurring APN promoter with all or part of a heterologous promoter, so that the cells express APN polypeptide at higher levels. The heterologous promoter is inserted in such a manner that it is operatively linked to endogenous APN encoding sequences. [See, for example, PCT International Publication No. WO 94/12650, PCT International Publication No. WO 92/20808, and PCT International Publication No. WO 91/09955.] It is also contemplated that, in addition to heterologous promoter DNA, amplifiable marker DNA (e.g., ada, dhfr, and the multifunctional cad gene, which encodes for carbamyl phosphate synthase, aspartate transcarbamylase, and dihydroorotase) and/or intron DNA may be inserted along with the heterologous promoter DNA. If linked to the APN coding sequence, amplification of the marker DNA by standard selection methods results in co-amplification of the APN coding sequences in the cells.

Alternatively, APN expression may also be induced by treatment with compounds known to induce expression of APN in a cell, such as for example a treatment with basic fibroblast growth factor (bFGF) (Fontijn D et al., 2006, BRITISH JOURNAL OF CANCER, 94, 1627-1636), or with bestatin (Imamura, Nobutaka, 2000. Leukemia and lymphoma, 37, 663-667.

Cell Lines

As already adressed hereinbefore, the cells used in the methods of the invention include; primary cells isolated from small intestinal epithelial tissue, such as for example enterocyte preparations; or continuous cells including recombinant cell lines expressing APN.

In a first embodiment these cell lines consist of primary cell cultures of APN expressing cells, such as for example intestinal epithelial cells, or epithelial cells of the respiratory tract, endothelial cells, kidney cells, at synaptic junctions and on monocytes, macrophages, dendritic cells (DC) and granulocytes, activated T lymphocytes and the earliest stages of B- or T-cell differentiation, on proliferating granulo- and myeloprogenitors (CFU-GM), on malignant acute myeloblastic cells but also on lymphoblastic leukemia cells. APN is expressed on stem cells and during most development stages of myeloid cells and therefore it is generally considered as a myelomonocytic marker. It is highly expressed on DC precursors of myeloid or lymphoid origin as well as on differentiated DC. In a particular embodiment, the APN expressing cells are enterocyte preparations of small intestinal epithelial cells from a mammal, including, pig, human, rat, mouse, dog, cat, bovine or sheep; more in particular enterocyte preparations of small intestinal cells of the pig.

Cells that are cultured directly from an animal or person are known as "primary cells". With the exception of some derived from tumours, most primary cell cultures have limited lifespan. After a certain number of population doublings cells undergo the process of senescence and stop dividing, while generally retaining viability. Methods for growing suspension and adhesion cultures of primary cells are known to the person skilled in the art, such as for example described in "General Techniques of Cell Culture", Maureen A. Harrison and Ian F. Rae, Cambridge University Press 2007.

As used in the methods of the present invention, the "primary cells" are derived from; intestinal epithelial cells, or epithelial cells of the respiratory tract, endothelial cells, kidney cells, at synaptic junctions and on monocytes, macrophages, dendritic cells (DC) and granulocytes, activated T lymphocytes and the earliest stages of B- or T-cell differentiation, on proliferating granulo- and myeloprogenitors (CFU-GM), on malignant acute myeloblastic cells but also on lymphoblastic leukemia cells. APN is expressed on stem cells and during most development stages of myeloid cells and therefore it is generally considered as a myelomonocytic marker. It is highly expressed on DC precursors of myeloid or lymphoid origin as well as on differentiated DC. In particular embodiments of the present invention, the "primary cells" are derived from enterocyte preparations of small intestinal epithelial cells from a mammal.

This in contrast to "continuous cells" also known as "an established" or "immortalized" cell line that has acquired the ability to proliferate indefinitely either through random mutation or deliberate modification, such as artificial expression of the telomerase gene. There are numerous well established cell lines representative of particular cell types.

In the context of the present invention, the continuous cells are either derived by immortalization from the primary cell cultures mentioned herein before or obtained from a well established continuous cell line treated, in particular by transfection with a nucleic acid sequence encoding APN, to yield a stable expression of the APN protein.

Several established methods exist for immortalizing mammalian cells in culture. Viral genes, including Epstein-Barr virus (EBV), Simian virus 40 (SV40) T antigen, adenovirus E1A and E1B, and human papillomavirus (HPV) E6 and E7 can induce immortalization by a process known as viral transformation. Although the process is reliable and relatively simple, these cells may become genetically unstable (aneuploid) and lose the properties of primary cells. For the most part, these viral genes achieve immortalization by inactivating the tumor suppressor genes that put cells into a replicative senescent state. The preferred method to immortalize cells is through expression of the telomerase reverse transcriptase protein (TERT), particularly those cells most affected by telomere length (e.g., human). This protein is inactive in most somatic cells, but when hTERT is exogenously expressed the cells are able to maintain telomere lengths sufficient to avoid replicative senescence. Analysis of several telomerase-immortalized cell lines has verified that the cells maintain a stable genotype and retain critical phenotypic markers.

The well established continuous cells used herein are typically selected from the group consisting of cells with epithelial characteristics such as for example IPEC-J2 cells, BHK-21 cells, 12MBr6, 293, 293T/17, 2CSFMEo, 3LL, 4MBr-5, 56FHTE8o, 6CSFMEo, 9HTEo-, A549, AK-D, A-72, Bing [CAK 8; CAK8), BHK, CaCo2, Ca Ski, CFNPE90-CF, CFPEo, CFSMEo, CHO, CHO-K1, COLO 205, CrFK, CuFi-1, DHD Pro.b, DLD-1, DoCl1 (S+L–), EPEC, FHs 74 Int, FL, FKCU, Fcwf-4, GPC-16, H69AR, HaK, HCT-15, HCT-116, HEK 293, HeLa, HeLa 229, HeLa S3, HeLa NR1, HEp-2, HL-60, HL-60R, HKB-11, HRT-18G, HT-29, IPEC-I, IEC-18, IEC-6, intestine 407, Kasumi-3, Kasumi-4, Kasumi-6, KU812, L2, L-132, LA-4, LLC-PK1, LLC-MK2, LoVo, LS123, LS 174T, MDCK, MDBK, MIAPaCa-2, MLE-12, MLE-15, MRC-5, NCI-H716, NCI-H747, NCI-H508, NCI-H498, NCI-H2126, NCI-H1688, NRK-52E, NuLi-1, OMK(637-69), PK(15), RKO, RK13, RPMI 2650, RL-65, SJPL, SK-RST, SNU-C2B, ST, SUP-B15, SW48, SW403, SW480, SW620, SW837, SW948, SW1116, SW1417, SW1463, T84, TCMK-1, VERO 76, WT 9-7, WT 9-12, W162, WiDr, WISH cells or cells derived from these cells; in particular IPEC-J2 cells, or BHK-21 cells.

Hence in a further embodiment the cell lines consist of continuous cells expressing APN.

Assays

Assays of the present invention can be designed in many formats generally known in the art of screening compounds for biological activity or for binding receptors.

Polypeptides of the present invention are responsible for one or more biological functions, including one or more disease states, in particular the diseases hereinbefore mentioned. It is therefore desirable to devise screening methods to identify compounds which mimic or which inhibit the function of the APN receptors in the mucosal uptake and subsequent intestinal mucosal immune response of antigens like F4

The assays of the present invention advantageously exploit the fact that ETEC fimbriae are high affinity ligands for APN receptor polypeptides and activate the APN receptors upon binding thereto.

Binding Assays

Therefore, the present invention includes methods of identifying compounds that specifically bind to APN receptor polypeptides, wherein said compounds may be ligands, agonists or antagonists of the APN receptor polypeptide. The assay methods of the present invention differ from those described in the art because the present assays incorporate at least one step wherein the interaction of E. coli fimbriae, in particular F4 fimbriae with the APN receptor is incorporated in the assay, either in assessing whether the test compound competes with the interaction of E. coli fimbriae and the APN receptor, or in comparing the interaction of the test compound and the APN receptor with the interaction of E. coli fimbriae and the APN receptor, for example by comparing the binding affinity. The specificity of binding can be shown by measuring the affinity of the compounds for cells expressing an APN receptor polypeptide on the surface thereof or affinity for membranes of such cells.

Thus, the present invention provides on the one hand a method for a method of identifying and obtaining a test compound capable of binding an APN receptor comprising: a) incubating a source containing an APN receptor or a functional fragment thereof, with i) E coli fimbriae ii) said test compound; and b) measuring the effect of the test compound on the amount of E. coli fimbriae bound to the receptor.

On the other hand it provides a method for a method of identifying and obtaining a test compound capable of binding an APN receptor comprising: a) incubating a source containing an APN receptor or a functional fragment thereof, with i) E coli fimbriae or ii) said test compound; and b) comparing the interaction of the test compound and the APN receptor with the interaction of E. coli fimbriae and the APN receptor.

In a preferred embodiment of the aforementioned methods, the E coli fimbriae, consist of F4 fimbriae, more in particular F4ac or F4ab fimbriae, even more in particular F4ac fimbriae.

In a further embodiment of the present invention, the APN containing source is selected from the group consisting of; i) an isolated and purified APN protein or a functional fragment thereof; ii) cells expressing on the surface thereof APN protein or a functional fragment thereof; or iii) membrane preparations of cells expressing on the surface thereof the APN protein or a functional fragment thereof.

APN expressing cells useful in the aforementioned methods have been discussed in more detail hereinbefore and membrane preparations to be used in the aforementioned methods are known to the person skilled in the art and include for example the Brush Border Membrane Vesicles described in the examples hereinafter.

In particular objects of the present invention the APN containing source comprises a mammalian APN as defined hereinbefore, more in particular porcine APN (pAPN).

The screening method may simply measure the binding of a candidate compound to the polypeptide, or to cells or membranes bearing the polypeptide, or a fusion protein thereof by means of a label directly or indirectly associated with the candidate compound. Alternatively, the screening method may involve competition with a labeled competitor. In a preferred embodiment, this labeled competitor is a ligand known to bind to APN such as F4 fimbriae. In particular using the E. coli F4ac fimbriae as ligand. The revealing label may be any suitable label which allows the polypeptide to be detected. Suitable labels include fluorochromes, e.g. 5(6)-carboxy-fluorescein-N-hydroxysuccinimide ester (FLUOS), radioisotopes, e.g. $^{125}$I, enzymes, antibodies, polynucleotides and linkers such as biotin. In particular FLUOS-labeled F4 fimbriae; more in particular FLUOS-labeled F4ac fimbriae are used.

Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed.

Alternatively, membrane preparations can be used in the screening methods of the present invention. Membrane preparations of APN expressing cells can be used in conventional filter-binding assays (eg. Using Brandel filter assay equipment) or in high throughput Scintillation Proximity type binding assays (SPA and Cytostar-T flashplate technology; Amersham Pharmacia Biotech) to detect binding of radio-labelled F4 fimbriae ligands (including radioionidated F4 fimbriae using $^{123}$Iodium) and displacement of such radio-ligands by competitors for the binding site. Radioactivity can be measured with Packard Topcount, or similar instrumentation, capable of making rapid measurements from 96-, 384-, 1536-microtitre well formats. SPA/Cytostar-T technology is particularly amenable to high throughput screening and therefore this technology is suitable to use as a screen for compounds able to displace standard ligands.

Another approach to study binding of ligands to APN protein in an environment approximating the native situation makes use of a surface plasmon resonance effect exploited by the Biacore instrument (Biacore) or similar instrumentation. APN comprising membrane preparations or whole cells could be attached to the biosensor chip of a Biacore and binding of ligands examined in the presence and absence of test compounds to identify competitors of the binding site.

Functional Assays

As shown in the examples hereinafter, F4 binding to the APN receptor is followed by clathrin-dependent internalization, and transcytosis across the mucosal barrier.

The effect of a compound on the cellular internalization could be examined using an APN expressing cells (e.g. pAPN transfected BHK-21 cells) which will be incubated with detectably labeled-F4 fimbriae or a detectably labeled APN specific antibody. Such a method to identify and obtain a compound capable to modulate the cellular internalization, comprises the steps of; (a) incubating APN expressing cells with detectably labeled E coli fimbriae or detectably labeled APN specific antibody in the presence and absence of the compound to be tested; and (b) determine the effect of the compound on the clathrin-dependent APN internalization and transcytosis by said cells.

As provided in the examples hereinafter, in one embodiment the E coli fimbriae are fluorescently labeled and the internalization is determined using clathrin specific antibodies, i.e. pAPN transfected BHK-21 cells are incubated with fluorescein labeled F4 fimbriae at 37° C. to allow internalization. Either cells have been preincubated with the compound or incubation with the compound occurs together with the labeled ligand. After 30 min. of incubation with the labeled ligand, the unbound and not-endocytosed ligand is washed away and cells are fixed with 3% paraformaldehyde, permeabilized with 0.1% Triton X-100 and stained with 1:30 mouse anti-clathrin heavy chain IgM antibodies (clone CHC 5.9, ICN Biomedicals Inc., Belgium) in PBS$^+$ at 37° C. Afterwards, cells are washed again and incubated with a 1:100 dilution of rat anti-mouse IgM Texas Red (Molecular Probes, Eugene, Oreg., USA) at 37° C. After a last washing cells are mounted and analyzed by confocal microscopy.

Accordingly, the present invention provides a method of identifying and obtaining a test compound (hereinafter also referred to as a binding agent or APN specific target molecule) capable of modulating the activity, i.e. clathrin-mediated endocytosis of the APN receptor comprising: a) incubating a source containing APN or functional fragments thereof, with said test compound; b) measuring the effect of the test compound on the activity of the APN receptor; and c) compare this effect with the activity of the APN receptor upon binding of E coli fimbriae or an APN-specific antibody, in particular F4 fimbriae.

The effect of the test compound on the clathrin-mediated endocytosis is typically assessed by determining the transfer of the compound through the APN containing source in the presence and absence of inhibitors that block clathrin-mediated endocytosis such as for example hypertonic sucrose, amantadine-HCl, dynamin inhibitory peptide, and cytochalasin D. Transfer of the test compound can be assessed using art known methodologies, such as for example described in Advanced drug Delivery Reviews, 2001, Vol 48(2-3); 173-193 and either exploit physicochemical characteristics of the test compound per se, such as mass spectrometry, UV spectrometry or a colorimetric determination; or exploit the physicochemical characteristics of a label or of the interaction of said compound with a revealing agent such as in an enzymatic determination, immunological determination, fluorescent or a radiological determination. Other examples are ELISA's, Immunoassays, RIA's, filter-binding assays, scintillation proximity assays (SPA), Cytostar-T technology, immunoprecipitation assays or the use of a surface plasmon resonance effect exploited by the Biacore instrument.

In a preferred embodiment, the test compound, the E coil fimbriae or APN-specific antibody in the aforementioned methods is detectably labeled. The revealing label may be any suitable label which allows the molecule or polypeptide to be detected. Suitable labels include fluorochromes, e.g. 5(6)-carboxy-fluorescein-N-hydroxysuccinimide ester (FLUOS), radioisotopes, e.g. $^{125}$I, enzymes, antibodies, polynucleotides and linkers such as biotin. More in particular FLUOS-labeled F4 fimbriae, even more in particular FLUOS-labeled F4ac fimbriae are used.

It will be readily appreciated by the skilled artisan that the discovery of the interaction of F4 fimbriae with APN may also be used in a method for the structure-based or rational design of an agonist or antagonist of the polypeptide, by: a) probing the structure of the ligand binding site on APN with F4 fimbriae; b) identifying contacting atoms in the ligand binding site of the APN receptor that interact with the F4 ligand during binding; c) design test compounds that interact with the atoms identified in (b) to modulate the activity of the APN receptor; and d) contact said designed test compound with a source containing APN or a functional fragment thereof, to measure the capability of said compound to modulate the APN activity.

It will be further appreciated that this will normally be an iterative process.

Binding Agents

Thus the invention further provides novel binding agents, including modulatory agents obtained by an assay according to the present invention, and compositions comprising such agents. Said agents which bind to the APN receptor and which mimic the interaction of F4 fimbriae with APN, herein also referred to as APN specific target molecules, are characterized in that they bind to the APN receptor, optionally through the α2-3,6,8,9 linked sialic acids found on APN; and in that they induce a clathrin-mediated endocytosis of APN. Such agents or compositions, including chimeric molecules comprising said APN specific target molecules, may be used in methods of treating conditions associated with a mucosal immune response, in particular an intestinal mucosal immune response and such use forms a further aspect of the invention.

Such conditions may include all kind of infections of the gastrointestinal tract (parasitic, viral, bacterial, mycotic, yeast infections), food allergies, Crohn's disease and Inflammatory and Irratable Bowel disease and IgA deficiencies. In particular said condition consists of diarrhoea, more in particular bacterial diarrhoea.

It is thus an object of the present invention to provide an APN specific target molecule wherein said molecule is characterized in that;

- it specifically binds the APN receptor, in particular the complex N-linked glycans of the glycosilated APN receptor, more in particular through the through the α2-3,6,8,9 linked sialic acids bounds thereto;
- it induces a clathrin-mediated endocytosis of APN; and wherein said agent is not *E. coli* F4ac.

Thus the invention further provides novel binding agents, including modulatory agents obtained by an assay according to the present invention, and compositions comprising such agents. Agents which bind to the APN receptor and which mimic the interaction of F4 fimbriae with APN, i.e. in that they bind through the α2-3,6,8,9 linked sialic acids found on APN, may be used in methods of treating conditions associated with a mucosal immune response, in particular an intestinal mucosal immune response and such use forms a further aspect of the invention.

Such conditions may include all kind of infections of the gastrointestinal tract (parasitic, viral, bacterial, mycotic, yeast infections), food allergies, Crohn's disease and Inflammatory and Irratable Bowel disease and IgA deficiencies. In particular said condition consists of diarrhoea, more in particular bacterial diarrhoea.

Furthermore, the agents may be used to deliver antigens/therapeutics, i.e. immunomodulators to the intestinal submucosa or the intestinal mucosa-associated lymphoid tissue; in particular for inducing an antigen specific intestinal mucosal immune response; more in particular to yield an oral immunization against the antigen delivered with said agents.

The agents may be administered an effective amount of an agent of the invention. Since many of the above-mentioned conditions are chronic and often incurable, it will be understood that "treatment" is intended to include achieving a reduction in the symptoms for a period of time such as a few hours, days or weeks, and to include slowing the progression of the course of the disease.

Such agents may be formulated into compositions comprising an agent together with a pharmaceutically acceptable carrier or diluent.

In this regard, in preferred embodiments, the drug delivery compositions comprise a particle of variable dimension and known as a microsphere, micropartile, nanoparticle, nanosphere or liposomes. In a particular form, said particle consists of biodegradable and/or biocompatible microsphere, micropartile, nanoparticle, nanosphere or liposemes; and more in particular, biodegradable and/or biocompatible nanoparticles such as superparamagnetic iron oxide nanoparticles (MION), polyelectrolyte capsules or nanoparticles made with biodegradable polymers like Gantrez or the copolymer methyl vinyl ether and maleic anhydride.

Such relatively homogenous essentially spherical particulate formulations containing an active agent can be formed by contacting an aqueous phase containing the active and a polymer and a nonaqueous phase followed by evaporation of the nonaqueous phase to cause the coalescence of particles from the aqueous phase as taught in U.S. Pat. No. 4,589,330. Porous microparticles can be prepared using a first phase containing active and a polymer dispersed in a continuous solvent and removing the solvent from the suspension by freeze-drying or dilution-extraction-precipitation as taught in U.S. Pat. No. 4,818,542. Preferred polymers for such preparations are natural or synthetic copolymers or polymer selected from the group consisting of gleatin agar, starch, arabinogalactan, albumin, collagen, polyglycolic acid, polylactic aced, glycolide-L(−) lactide poly(episilon-caprolactone, poly(epsilon-caprolactone-CO-lactic acid), poly(epsilon-caprolactone-CO-glycolic acid), poly(β-hydroxy butyric acid), polyethylene oxide, polyethylene, poly(alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly preferred polymers are polyesters, such as polyglycolic acid, polylactic aced, glycolide-L(−) lactide poly (episilon-caprolactone, poly(epsilon-caprolactone-CO-lactic acid), and poly(epsilon-caprolactone-CO-glycolic acid. Solvents useful for dissolving the polymer and/or the active include: water, hexafluoroisopropanol, methylenechloride, tetrahydrofuran, hexane, benzene, or hexafluoroacetone sesquihydrate. The process of dispersing the active containing phase with a second phase may include pressure forcing the first phase through an orifice in a nozzle to effect droplet formation.

The agent may in the form of a physiologically functional derivative, such as an ester or a salt, such as an acid addition salt or basic metal salt, or an N or S oxide. Compositions may be formulated for any suitable route and means of administration.

Pharmaceutically acceptable carriers or diluents include those used in formulations suitable for oral, rectal, nasal, inhalable, topical (including buccal and sublingual), vaginal or parenteral (including subcutaneous, intramuscular, intravenous, intradermal, intrathecal and epidural) administration. The choice of carrier or diluent will of course depend on the proposed route of administration, which, may depend on the agent and its therapeutic purpose. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For solid compositions, conventional non-toxic solid carriers include, for example, pharmaceutical grades of mannitol, lactose, cellulose, cellulose derivatives, starch, magnesium stearate, sodium saccharin, talcum, glucose, sucrose, magnesium carbonate, and the like may be used. The active compound as defined above may be formulated as suppositories using, for example, polyalkylene glycols, acetylated triglycerides and the like, as the carrier. Liquid pharmaceutically administrable compositions can, for example, be prepared by dissolving, dispersing, etc, an active compound as defined above and optional pharmaceutical adjuvants in a carrier, such as, for example, water, saline aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound (s) in an amount effective to alleviate the symptoms of the subject being treated.

Dosage forms or compositions containing active ingredient in the range of 0.25 to 95% with the balance made up from non-toxic carrier may be prepared.

For oral administration, a pharmaceutically acceptable non-toxic composition is formed by the incorporation of any of the normally employed excipients, such as, for example, pharmaceutical grades of mannitol, lactose, cellulose, cellulose derivatives, sodium crosscarmellose, starch, magnesium stearate, sodium saccharin, talcum, glucose, sucrose, magnesium, carbonate, and the like.

Such compositions take the form of solutions, suspensions, nanoparticles, tablets, pills, capsules, gellules, powders, sustained release formulations and the like. Such compositions may contain 1%-95% active ingredient, more preferably 2-50%, most preferably 5-8%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions.

Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, triethanolamine sodium acetate, etc.

The percentage of active compound contained in such parental compositions is highly dependent on the specific nature thereof, as well as the activity of the compound and the needs of the subject. However, percentages of active ingredient of 0.1% to 10% in solution are employable, and will be higher if the composition is a solid which will be subsequently diluted to the above percentages. Preferably, the composition will comprise 0.2-2% of the active agent in solution.

This invention will be better understood by reference to the Experimental Details that follow, but those skilled in the art will readily appreciate that these are only illustrative of the invention as described more fully in the claims that follow thereafter. Additionally, throughout this application, various publications are cited. The disclosure of these publications is hereby incorporated by reference into this application to describe more fully the state of the art to which this invention pertains.

EXAMPLES

The following examples illustrate the invention. Other embodiments will occur to the person skilled in the art in light of these examples.

Example 1

Identification of Aminopeptidase N as a Potential F4 Receptor

Methods
In Vitro Villous Adhesion Assay for F4R Characterisation of the Piglets

Thirteen pigs from 13 different sows and 13 different boars of 5 different pig farms in Northern Belgium were tested. In order to determine the presence or absence of the F4R on brush borders of small intestinal villous enterocytes, an in vitro villous adhesion assay was performed as described by Van den Broeck (1999). Adhesion of more than 5 bacteria per 250 μm villous brush border length was noted as positive. 89
F4 Purification and Labelling of F4 with Fluorescein 91

F4 fimbriae were purified as described by Van den Broeck (1999). Briefly, fimbriae were isolated by homogenizing the bacterial suspension of strain *E. coli* GIS26 (serotype O149: K91, F4ac+, LT+STa+STb+) using an Ultra Turrax (Janke & Kunkel, I K A Labortechnik, Staufen, Germany), followed by a purification using 2 centrifugation steps (20,000×g, 40 min, 4° C.) and a precipitation step with 40% ammonium sulphate. Thereafter, the pellet was dissolved and dialysed overnight against PBS. The F4 was labelled with 5(6)-carboxyfluorescein-N-hydroxysuccinimide ester (FLUOS, 480 Da) using the fluorescein labelling kit (Roche Diagnostics GmbH, Mannheim, Germany). The molar reaction ratio F4:FLUOS used was 1:10. Remaining non-reacted-FLUOS was blocked by adding 1:100 of 0.1 M glycin in PBS to reach a final concentration of 1 mM glycin (incubation 1 h at 18° C.), which was subsequently removed by dialysis against PBS using a membrane with a cut off of 14 kDa. Before use, the binding of the FLUOS-labeled-F4 to the F4R on villous brush border enterocytes was tested in vitro.
Enterocyte Preparations Small intestinal epithelial cells from the pig were isolated by the method of Lundqvist (1992). The small intestine (jejunum) was washed twice with Krebs-Henseleit buffer (0.12 M NaCl, 0.014 M KCl, 0.001 M KH2PO4 and 0.025 M NaHCO3 adjusted to pH 7.4). The segment was inverted and cut into small fragments. To remove the enterocytes from the tissue fragments, the fragments were incubated in Hanks' balanced salt solution (HBSS) with 1 mM dithiotreitol (DTT, Sigma-Aldrich Chemie GmbH, Steinheim, Germany) and 1.5 mM EDTA (Sigma-Aldrich Chemie GmbH, Steinheim, Germany) while shaking at 200 rpm for 30 min at 37° C. The cell suspension obtained was passed through organza to remove the mucus and centrifuged at 1,811×g for 10 min at 4° C. Enterocytes were washed 3 times in HBSS with 0.1 mM of the protease inhibitor, phenylmethylsulfonyl fluoride (PMSF, Sigma-Aldrich Chemie GmbH, Steinheim, Germany). The purity of the samples was analyzed by light microscopy on the basis of the normal morphology for enterocytes; our samples contained 85% enterocytes.

Membrane Preparations

Brush border membrane vesicles (BBMV) of the small intestine were prepared from the F4R+ and F4R− pigs by the method of Kessler (1978) with a slight modification. Enterocytes were washed twice in PBS with 0.1 mM PMSF and were resuspended in Tris-HCl buffer (2 mM, pH 7.2) containing 50 mM mannitol in ratio 3:1 (vol/vol) whereafter cells were homogenized for 2 min with an Ultra Turrax (Janke & Kunkel, I K A Labortechnik, Staufen, Germany). Subsequently, CaCl2 was added to the homogenate to a final concentration of 10 mM and placed on ice for 15 min. Then the homogenate was centrifuged at 27,000×g for 30 min and washed with Tris buffer (pH 7.5) containing 50 mM mannitol and 10 mM HEPES and centrifuged again. The pellet was resuspended in the same buffer and used for the study. The protein concentration of the obtained BBMV was determined using the bicinchoninic acid (BCA) reaction with bovine serum albumin (BSA) as standard (ICN Biomedicals, Belgium).

Immobilization of F4 Fimbriae on Sensor Chip

The interaction between the F4ac fimbriae and BBMV or enterocytes of F4R+ and F4R− pigs was analyzed with the BIAcore®2000 biosensor (Uppsala, Sweden) using the CM3 chip. This has a short carboxymethyldextran surface to allow immobilization of F4 fimbriae via free NH2-groups using an amine-coupling kit (Biacore, Uppsala, Sweden) containing N-hydroxysuccinimide (NHS), N-ethyl-N'-[(3-dimethylamino)-propyl]-carbodiimide hydrochloride (EDC) and ethanolamine-HCl. Hereto, 100 µl of a mixture of NHS:EDC (1:1) was injected at a flow rate of 10 µl/min at 25° to activate the dextran matrix on the sensor chip, followed by F4ac at a concentration of 100 µg/ml in 0.1 M glycine buffer pH 2.3 until the amount (mol) of immobilized F4 equilized more than 500 resonance units (RU). Thousand RU corresponds to a change in the surface concentration of 1 ng/mm2 (Stenberg 1991). Subsequently, the remaining active sites of the matrix were blocked with 1 M ethanolamine-HCl and washed with HBS-N (0.01 M HEPES, 0.15 M NaCl). Two controls were performed, one flow cell was activated and subsequently blocked without immobilization of F4ac fimbriae (reference, blanco) and a second one by immobilizing a flow cell with 100 µl wheat germ agglutinin (WGA, Aniara, Ohio) at a concentration of 50 µg/ml in 10 mM sodium acetate buffer pH 4.5 at a flow rate of 5 µl/min at 25° to check the specificity of the bestatin inhibition. All samples used in further experiments were diluted in HBS-N buffer, which also served as running buffer during the experiments.

Determining the Interaction Between F4 and the F4 Receptor

The first approach was to pre-incubate the F4R+ and F4R− enterocytes or BBMV with 0, 50 and 100 µg/ml F4ac fimbriae, while gently shaking. After 1 h pre-incubation at room temperature, a gentle short spin centrifugation was performed. Subsequently, the supernatant was discharged, and the samples were adjusted to the start volume (6.105 enterocytes/ml or 100 µg BBMV/ml) and injected as described above. The second approach was to block the binding between F4ac and F4R+ enterocytes or BBMV. Hereto, F4R+ enterocytes or BBMV were pre-incubated with 0, 1 mM and 10 mM bestatin, while gently shaking. After 1 h pre-incubation at room temperature, the samples were injected as described above. As a control, F4R− enterocytes and BBMV were also tested.

To check the specificity of blocking of bestatin, F4R+ and F4R− enterocytes or BBMV were pre-incubated with 0, 1 mM and 10 mM bestatin, while gently shaking for 1 hour at room temperature and injected in the WGA coated flow cell. All these experiments were performed on BBMV and enterocytes isolated from different pigs: F4R+ enterocytes (n=3); F4R− enterocytes (n=2); F4R+ BBMV (n=2); F4R− BBMV (n=2).

Two-Dimensional Electrophoresis

For the first dimension iso-electric focusing, 11 cm ReadyStrip IPG Strips with pH gradient 4-7 were used (Bio-Rad, Hercules, Calif., USA). Brush border membrane proteins (500 µg) were incorporated into the IPG strips by in-gel rehydration (Sanchez 1999) in a total of 250 µl rehydration solution (7 M urea, 2 M thiourea, 2% w/v CHAPS, 2% carrier ampholytes and a trace of bromophenol blue) for at least 6 hours. Strips were iso-electrically focussed on the Protean IEF System (Bio-Rad, Hercules, Calif., USA) at 18° C., using 100 V for 30 min (linear ramping), 250 V for 30 min (lineair ramping), 1000 V for 30 min (lineair ramping), rapid ramping to 8000 V in 2 h and steady state at 8000 V for 25000 Vh. After isoelectric focussing, the strips were treated with equilibration solution (50 mM TrisHCl pH 6.8, 6 M urea, 20% v/v glycerol, 2% w/v SDS) supplemented with 1.5% w/v DTT for 15 min followed by 15 min in equilibration solution supplemented with 4% w/v iodoacetamide. The second dimension SDS-PAGE was performed on a vertical electrophoresis system (Bio-Rad, Hercules, Calif., USA) using Laemmli 10% resolving polyacrylamide gels and run in sets of 2 at 150 V for 30 min followed by 200 V until the bromophenol blue front reached the edge of the gel. One of the gels was stained with Sypro Ruby (Molecular Probes, Eugene, Oreg., USA) for 3 hours. After staining, the gels were washed twice in 10% methanol, 7% acetic acid for 15 min to obtain low residual matrix background. A protein standard marker (MagicMark XP, Invitrogen) was loaded on each gel.

Immunoblotting

The remaining gel was used for immunoblotting. The proteins were transferred to nitrocellulose membranes by wet blotting using the Trans-Blot Cell (Bio-Rad, Hercules, Calif., USA) at a constant voltage of 50 V for 3 hours. Prior to blotting, both the polyacrylamide gel and nitrocellulose membranes were incubated in CAPS 1× (pH 11) for at least 15 min. Ponceau S visualization was performed in order to check the blotting efficiency and to verify the 2-D pattern. This stained membrane was scanned, digitized and used as a reference image of the most abundant proteins. The membrane was subsequently destained, blocked with 5% non-fat dry milk/PBS/0.3% Tween-80 overnight at 4° C., incubated for 1 hour at room temperature with 2 µg/ml F4. Thereafter, the membrane was incubated with the F4 specific MAb (Van der Stede 2002) for 1 hour. Subsequently, the membrane was incubated with rabbit anti-mouse horseradish peroxidase conjugate (DAKO, Glostrup, Denmark) for 1 hour (dilution 1:1000) and incubated for 5 min with ECL Western blotting substrate (Pierce Biotechnology Inc, Rockford, Ill., USA). In between each step, the membrane was washed three times with PBS/0.3% Tween-20 for 5 minutes.

In-Gel Digestion and Peptide Sample Preparation

Protein spots were excised from the gel and in-gel digested with sequence grade modified trypsin (porcine) (Promega, Madison Wis., USA). Two washing steps were performed by adding 25 mM NH4HCO3 and 50% acetonitrile for 10 min. A volume of 10 mM DTT in 25 mM NH4HCO3 sufficient to cover the gel pieces was added and the proteins were reduced for 10 min at 56° C. After cooling to room temperature for 20 min, the DTT solution was replaced with the same volume of 100 mM iodoacetamide in 25 mM NH4HCO3. After 45 min incubation at ambient temperature in the dark with occasional shaking, the gel pieces were washed once with 25 mM NH4HCO3 and 50% acetonitrile for 10 min, dehydrated by addition of acetonitrile and completely dried in a vacuum centrifuge. The gel pieces were digested for 30 min in 10 ng/µl trypsin on ice. After incubation overnight at 37° C., peptides were extracted first with 50% acetonitrile and another change with 100% acetonitrile (30 min for each change). The liquid phase was pooled and completely dried in a vacuum centrifuge.

Identification by ESI Mass Spectrometry

Dried peptide mixtures were solubilized in 10 µl 0.1% formic acid and injected on an on-line nano LC system using column switching (LC Packings, Sunnyvale, Calif., USA) coupled to a Q-TOF Ultima mass spectrometer (Waters, Milford, USA) fitted with an orthogonal Z-spray. The data were acquired using automatic function switching software from MassLynx 4.0 (Waters, Milford, USA). Fragmentation spectra, resulting from tandem mass spectrometry were processed by ProteinLynx Global Server v2.2.5 software (Waters, Milford, USA). The resulting pkl files were searched against the Swiss-prot database using the MASCOT search engine (http://www.matrixscience.com).

Cell Line and Culture Conditions

The BHK-21 and pAPN transfected BHK-21 cells were kindly gifted from Dr. Enjuanes and Dr. Delmas. The BHK-21 cells were cultured in DMEM with 5% FCS, 1% L-Glu, 1% P/S, 1% sodiumpyruvate (Gibco BRL, Life Technologies Inc., Paisley, Scotland), 1% non-essential amino acids (Gibco BRL, Life Technologies Inc., Paisley, Scotland). The pAPN transfected BHK-21 cells were grown in the same medium supplemented with 1.5 mg/ml geneticin G418 (Sigma-Aldrich Chemie GmbH, Steinheim, Germany).

Treatment with Different Glycosidases

To remove sialic acid from the pAPN, 2 mg/ml BBMV from F4R+ pigs were incubated with soluble neuraminidase from *Arthrobacter urefaciens* (Calbiochem, specific for α2-3,6,8,9 linked sialic acid) for 3 hours at 37° C. according to the manufacturer's instructions. Fetuin, a sialic acid containing protein was used as a positive control and the buffer in which the neuraminidase was provided, was used as a negative control. Brush border membrane vesicles from F4R+ pigs were treated with N-glycosidase F (NEB, Beverly, Mass.) or with endoglycosidase H (NEB Beverly, Mass.) according to the manufacturer's instructions to remove all N-glycans (high mannose and complex, sialic acid containing glycans) or N-glycans of the high mannose type, respectively. RNAse B was used as a positive control and the buffer in which the enzyme was provided, was used as a negative control.

Brush border membrane vesicles from F4R+ pigs were treated with variable concentrations of NaIO4 (Sigma-Aldrich Chemie GmbH, Steinheim, Germany) in 50 mM sodiumacetate, pH 4.5, at 37° C. in the dark. Reactions were stopped by the addition of ethylene glycol to a final concentration of 20 mM. Brush border membrane vesicles from F4R− pigs were treated with the same glycosidases and were used as a negative control.

Endocytosis Assay and Chemical Inhibitors

The BHK and pAPN-BHK cells were incubated with 25 µg FLUOS-labeled-F4 for 1 h at 4° C. to allow attachment, but no internalization. Cells were then washed with PBS supplemented with 0.1 mM CaCl2 and 1 mM MgCl2 (PBS+) to remove unbound FLUOS-labeled-F4 and shifted to 37° C. to start endocytosis. After different time intervals, cells were fixed with 3% paraformaldehyde (PF), permeabilized with 0.1% Triton X-100 and stained with 200 nM phalloidin-Texas Red (Molecular Probes, Eugene, Oreg., USA) in PBS+ for 1 h at 37° C. To analyze the effect of different inhibitors on endocytosis, cells were incubated with different concentrations of each inhibitor (Table 1). Inhibitors were added 30 min before incubation with FLUOS-labeled-F4 (25 µg). Cells were fixed with 3% PF at the indicated times. For each concentration of the chemical inhibitors, the viability of the cells was analyzed by flow cytometry after the addition of 10 µg propidium iodide (Molecular Probes, Eugene, Oreg., USA). The number of vesicles internalized in the cells was counted using confocal microscopy. Confocal images were acquired using a Leica TCS SP2 laser scanning spectrum confocal system (Leica Microsystems), using an argon 488-nm laser line and a Gre/Ne 543-nm laser line to excite FITC and Texas Red respectively. Images were merged using Leica confocal software.

TABLE 1

Inhibitors used in the study.

| Inhibitor | Function | Concentrations |
| --- | --- | --- |
| Amantadine | Interferes with clathrin-coated-pit invagination at the plasma membrane | 0-500 µM |
| Dynamin | inhibitory peptide Interferes with clathrin- and caveolae-mediated endocytosis and phagocytosis | 0-50 µM |
| Latrunculin B | Disrupts actin polymerization | 0-50 µM |
| Nystatin | Interferes with caveolae-mediated endocytosis | 0-100 µM |
| Cytochalasin D | Inhibits G-actin polymerization to F-actin Inhibits budding of clathrin-coated vesicles | 0-100 µM |

Treatment with Bestatin

To block the internalization of FLUOS-labeled-F4, 50 µM bestatin, an inhibitor of aminopeptidase N (Sigma-Aldrich Chemie GmbH, Steinheim, Germany) was incubated with BHK-21 or pAPN transfected BHK-21 cells 3 hours before addition of 25 µg FLUOS-labeled-F4. Afterwards, cells were washed 3 times with PBS. The BHK-21 or pAPN transfected BHK-21 cells were analyzed by flow cytometry with a FACScanto using CellDiva software (BD Biosciences). Ten thousand cells were analysed for each sample, and three parameters were used for further analysis: forward light scattering, sideward light scattering and green fluorescence. The median fluorescence intensity was used to measure the amount of FLUOS-labeled-F4 to the cells.

The inhibition with bestatin was also performed on villi of F4R+ pigs. A 15 cm long intestinal segment was excised of the mid jejunum at the moment of slaughter. The segment was washed twice with PBS and once with Krebs-Henseleit buffer (0.12 M NaCl, 0.014 M KCl, 0.001 M KH2PO4 and 0.025 M NaHCO3 adjusted to pH 7.4) containing 1% vol/vol formaldehyde at 4° C. Subsequently, the villi were scraped off with glass slides and washed 4 times in Krebs-Henseleit buffer without formaldehyde. Different concentrations of bestatin were added to the villi for 3 hours before addition of 25 µg FLUOS-labeled F4. Afterwards, villi were washed 3 times with Krebs-Henseleit buffer and evaluated by conventional fluorescence microscopy. Villi of F4R− pigs were used as a control.

Colocalization of Clathrin

The BHK-21 and pAPN transfected BHK-21 cells were incubated with 25 µg FLUOS-labeled-F4 at 37° C. to allow internalization. After 30 minutes, cells were washed with PBS+ and fixed with 3% PF, permeabilized with 0.1% Triton X-100 and stained with 1:30 mouse anti-clathrin heavy chain IgM antibodies (clone CHC 5.9, ICN Biomedicals Inc., Belgium) in PBS+ for 1 h at 37° C. Afterwards, cells were washed 3 times with PBS+ and incubated with a 1:100 dilution of rat anti-mouse IgM Texas Red (Molecular Probes, Eugene, Oreg., USA) for 1 h at 37° C. Finally, cells were washed with PBS+, mounted and analyzed by confocal microscopy.

Results

Surface Plasmon Resonance Analysis of F4 Binding to its Receptor

To determine the interaction of F4ac fimbriae with the F4R on enterocytes and brush border membrane vesicles (BBMV) of F4R+ and F4R− pigs, purified F4ac fimbriae were immobilized on a CM3 sensor chip (800 to 1300). Subsequently the enterocytes or vesicles of different F4R+ and F4R− pigs were examined for their F4-specific binding to immobilized F4ac fimbriae.

F4R+ enterocytes and F4R BBMV were able to bind to the F4 fimbriae, This interaction was stable since no dissociation was observed during flushing with running buffer. On the other hand, no interaction was observed using F4R− enterocytes or F4R− BBMV Enterocytes or BBMV of F4R+ pigs were pre-incubated with different concentrations of purified F4ac fimbriae, to test the specificity of the F4ac fimbriae binding. F4 fimbriae at a concentration of 50 and 100 µg/ml inhibited the adhesion of F4R+ BBMV to immobilized F4, resulting in 98±1.2% inhibition of binding of F4R+ BBMV to immobilized F4 (FIG. 2A). For F4R+ enterocytes, the F4 fimbriae at a concentration of 50 and 100 µg/ml inhibited the adhesion in a dose dependent way, resulting in 80±3.1% and 91±2.0% inhibition of binding of F4R+ enterocytes to immobilized F4, respectively.

To evaluate whether the observed binding between enterocytes or BBMV and immobilized F4 fimbriae was due to an interaction between F4ac and pAPN on the enterocytes or BBMV, bestatin, a potent inhibitor of pAPN was used. Bestatin binds with high affinity to pAPN and this complex is stable. Therefore bestatin may compete with F4 fimbriae for binding to pAPN. To investigate this, we pre-incubated BBMV and enterocytes of F4R+ pigs with different concentrations of bestatin for 1 hour at room temperature. Bestatin inhibited the binding between pAPN on F4R+ BBMV and F4ac in a dose dependent way. With a concentration of 1 mM or 10 mM bestatin resulted in 4±1.2% and 10±2% inhibition of adhesion, respectively. We could not increase the amount of bestatin, due to the concentration of ethanol in which the inhibitor was solved. The same concentrations added to enterocytes, showed a more pronounced effect, resulting in 22±3.3% and 72±1.0% inhibition of adhesion, respectively.

In order to check if bestatin has any general negative influence on BBMV and enterocytes of F4R+ pigs, BBMV and enterocytes were pre-incubated with different concentrations of bestatin (0 mM, 1 mM and 10 mM) and injected on immobilized WGA. No difference in interaction was observed for the pre-incubated BBMV or enterocytes and WGA at the different concentrations of bestatin (data not shown).

Identification of Aminopeptidase N as a Potential F4 Receptor.

The brush border membrane vesicles of 8 F4R+ and 5 F4R− pigs were separated by 2-D electrophoresis. Ponceau S stained membrane, the Sypro Ruby stained gel and the Western blots were compared and transparencies were prepared from the image. Protein spots from the Sypro Ruby stained gel, which aligned to spots on the Western blot were excised from the gel. Eight spots were reproducibly detected among the 8 F4R+ pigs and not in the 5 F4R− pigs.

These spots were subjected to identification by the combination of tryptic digestion and nano-LC-Q-TOF/MS analysis (Table 2). Mass spectrometric analysis allowed the identification of aminopeptidase N in spot 4, 5 and 6 with high confidence. Trypsin was used for our in-gel trypsin digestion and because these spots contained low amounts of protein (faint spots on the gel), the digest protease was identified. In the other spots, proteins were present that could be excluded as a receptor for F4ac binding like ubiquinol cytochrome C reductase (spots 1 and 2), which is a part of the mitochondrial respiratory chain and haemoglobin (spot 3), a pigment present in red blood cells. Based on these data, aminopeptidase N (pAPN) was further examined as a candidate receptor for F4ac.

Transfection of pAPN in BHK Cells Allows Binding of F4.

To investigate binding of F4 to pAPN, a comparison was made in F4ac binding capacity to untransfected and pAPN-transfected BHK-21 cells. Flow cytometry demonstrated that FLUOS-labeled F4 specifically binds to pAPN transfected BHK-21 cells with a mean fluorescence intensity of 2071±22, whereas no binding could be observed to untransfected BHK-21 cells (mean fluorescence intensity of only 196±12) (FIG. 1).

TABLE 2

Mass spectrometric analysis

| Spotnr. | Database protein name | Peptide Score | Protein Score | Expect | Peptide | Sequence coverage (%) | MWth (kDa) | pIth (pH) |
| --- | --- | --- | --- | --- | --- | --- | --- | --- |
| 1 | Ubiquinol cytochrome C reductase | 58 48 | 104 | 0.002 0.022 | R.IAEVDASVVR.E R.IPLAEWESR.I | 5 | 52.6 | 6.3 |
| 2 | Ubiquinol cytochrome C reductase | 48 | 56 | 0.022 | R.IPLAEWESR.I | 8 | 52.7 | 6.3 |

TABLE 2-continued

Mass spectrometric analysis

| Spotnr. | Database protein name | Peptide Score | Protein Score | Expect | Peptide | Sequence coverage (%) | MWth (kDa) | pIth (pH) |
|---|---|---|---|---|---|---|---|---|
| 3 | Hemoglobin beta subunit | 60 | 186 | 0.0014 | K.VLQSFSDGLK.H | 16 | 15.97 | 8.4 |
|   |   | 49 |   | 0.0016 | R.LLGNVIVVVLAR.R |   |   |   |
|   |   | 19 |   | 11 | R.LLVVYPWTQR.F |   |   |   |
|   |   | 57 |   | 0.0027 | K.VNVDEVGGEALGR.L |   |   |   |
| 4 | Aminopeptidase N | 58 | 502 | 0.0029 | R.DVSQAQNDLFK.T | 13 | 108.6 | 5.2 |
|   |   | 63 |   | 0.00091 | K.NNMDVGFGSGTR.A |   |   |   |
|   |   | 41 |   | 0.13 | K.EVVLNWFTEHS.- |   |   |   |
|   |   | 16 |   | 45 | K.NGVMQDHYWLR.D |   |   |   |
|   |   | 74 |   | 0.000048 | R.YLGYTLNPDLIR.K |   |   |   |
|   |   | 60 |   | 0.0015 | R.SALACSNEVWLLNR.Y |   |   |   |
|   |   | 69 |   | 0.00019 | K.QVEPLFQHFETLTK.N |   |   |   |
|   |   | 68 |   | 0.00028 | R.FSSEFELQQLEQFK.K |   |   |   |
|   |   | 38 |   | 0.15 | R.SSAFDYLWIVPISSIK.N |   |   |   |
|   |   | 17 |   | 7.8 | R.AQVIYDSFNLATAHMVPVTLALDNTLFLNGEK.E |   |   |   |
| 5 | Aminopeptidase N | 50 | 112 | 0.016 | R.DVSQAQNDLFK.T | 2 | 108.6 | 5.2 |
|   |   | 55 |   | 0.0033 | R.YLGYTLNPDLIR.K |   |   |   |
|   |   | 11 |   | 120 | R.FSSEFELQQLEQFK.K |   |   |   |
| 6 | Aminopeptidase N | 59 | 215 | 0.0019 | R.DVSQAQNDLFK.T | 5 | 108.6 | 5.2 |
|   |   | 11 |   | 150 | K.NNMDVGFGSGTR.A |   |   |   |
|   |   | 44 |   | 0.05 | K.EVVLNWFTEHS.- |   |   |   |
|   |   | 55 |   | 0.003 | R.YLGYTLNPDLIR.K |   |   |   |
|   |   | 50 |   | 0.015 | R.FSSEFELQQLEQFK.K |   |   |   |
| 7 | Trypsin precursor | 35 | 35 | 0.47 | K.LSSPATLNSR.V | 4 | 24.3 | 7.3 |
| 8 | Trypsin precursor | 47 | 47 | 0.033 | K.LSSPATLNSR.V | 4 | 24.3 | 7.3 |

Spotnr = these numbers refer to FIG. 1;
the peptide score = the ion score for the individual peptide;
the protein score = probability Mowse score reported by matrix science where p < 0.05 of the individual ions scores indicates identity or extensive homology;
Expect = the expectation value for the peptide match (the lower this value, the more significant the result);
Peptide = the sequence of the petide;
MWth = molecular weight of the protein spot obtained theoretically from the Swiss-Prot database (http://www.expasy.org);
pIth = isoelectric point of the protein spot obtained theoretically from the Swiss-Prot database (http://www.expasy,org)

Figure 2:
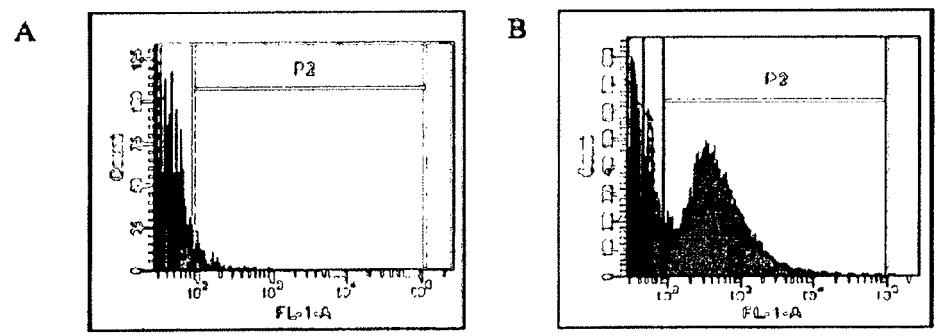
FIG. 2 Influence of bestatin on FLUOS-labeled-F4 binding. Flowcytometric histogram showing fluorescence intensity of BHK-21 (A) and pAPN transfected BHK-21 cells (B), treated wth bestatin (dotted line) before FLUOS-labeled-F4 incubation. As control, cells were incubated with FLUOS-labeled-F4 (grey shaded).

Blocking the interaction between F4 fimbriae and pAPN is proven in different ways. First, flow cytometry demonstrated that bestatin exhibit blocking capacity (FIG. 2). The mean fluorescence intensity of the BHK-21 cells after addition of FLUOS-labeled-F4 was 196±12. The pAPN transfected BHK-21 cells showed a reduction of mean fluorescence intensity from 2071±22 to 1001±15 after treatment of bestatin. Treatment with bestatin showed a clear influence on the binding of F4ac to pAPN.

Figure 3:
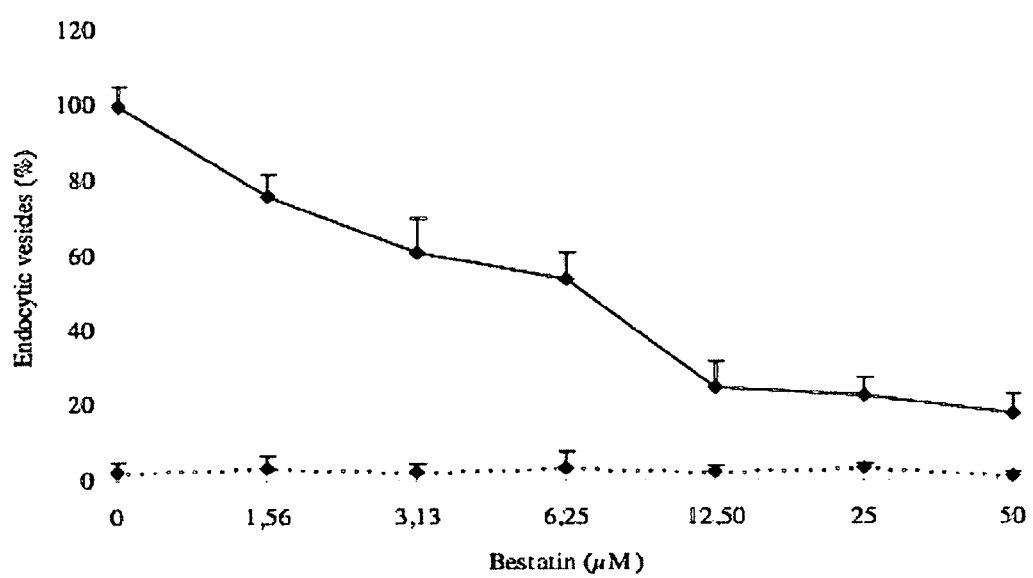
FIG. 3 Effect of bestatin on FLUOS-labeled-F4 internalization pAPN-BHK-21 (solid line) and BHK-21 (dotted line). Data represent the mean±standard deviation of 3 independent experiments.

Second, the interaction between FLUOS-labeled-F4 and pAPN on pAPN-BHK cells was also analysed using confocal microscopy. Different concentrations of bestatin were added 30 minutes before incubation with FLUOS-labeled F4. Bestatin clearly reduced FLUOS-labeled F4 internalization in a dose dependent way to a maximum of 18±5.3% at 50 μM, indicating the importance of pAPN during the internalization process (FIG. 3). As a negative control, BHK-21 cells were treated with the different concentrations of bestatin before adding FLUOS-labeled F4.

Binding of F4 to its Receptor is Dependent on Carbohydrate Moieties.

The BBMV of F4R+ and F4R− pigs were treated with various concentrations of NaIO4 during 30 min and 2 hours. The binding of F4 to the receptor in the F4R+ pig was greatly reduced by 25 mM NaIO4 after 30 min. Two hours treatment with periodate showed abolishing of the F4ac binding to the BBMV of F4R+ pigs indicating a role for carbohydrates in the binding of F4 to the receptor.

Since carbohydrate structures on the BBMV are important for the binding of F4, we further investigated if sialic acids on BBMV are involved in the binding of F4 by enzymatic removal of sialic acids from the surface of the BBMV. Treatment of BBMV with a recombinant neuraminidase from *Arthobacter urefaciens*, which removes α2-3,6,8,9 linked sialic acid, resulted in a reduction in reactivity of F4 to the BBMV of F4R+ pigs. This result shows that sialic acids on BBMV are involved in the binding of F4. As a control, fetuin was treated with neuraminidase and this sialic acid rich protein was completely deglycosylated (data not shown).

Sialic acids are terminal sugars that can be present on fully processed, complex N-linked glycans. High mannose N-linked glycans, on the contrary, do not possess sialic acids. To investigate if N-linked glycans containing sialic acids are involved in F4ac binding to intestinal epithelial cells, BBMV were treated with N-glycosidase F, which removes all N-glycans, or with endoglycosidase H, which removes only high mannose N-glycans. N-glycosidase F treatment of BBMV strongly reduced F4 binding. Treatment with endoglycosidase H had no effect on the binding (data not shown). Complex N-linked glycans are thus important for F4 binding to pAPN, whereas N-linked glycans of the high mannose type are not involved in the binding. RNAseB, a high mannose glycoprotein (1-3) with a single N-linked glycosylation site was used as a positive control for these endoglycosidases and showed a gel shift after deglycosylation (data not shown).

F4 Binding to its Receptor is Followed by Clathrin-Dependent Internalization

The mechanism of F4 endocytosis was analyzed using inhibitors that block clathrin- and caveolae-mediated endocytosis and phagocytosis (dynamin inhibitory peptide), clathrin-mediated endocytosis (amantadine-HCl and hypertonic sucrose), caveolae-mediated endocytosis (nystatin), an actin disrupting agent (latrunculin B) and an inhibitor that blocks G-actin polymerization to F-actin and budding of clathrin-coated vesicles (cytochalasin D). All the different concentrations of the chemical inhibitors which were used in this experiment, caused no significant decrease in cell viability, as analyzed by flow cytometry after incubation with propidium iodide.

Figure 4:
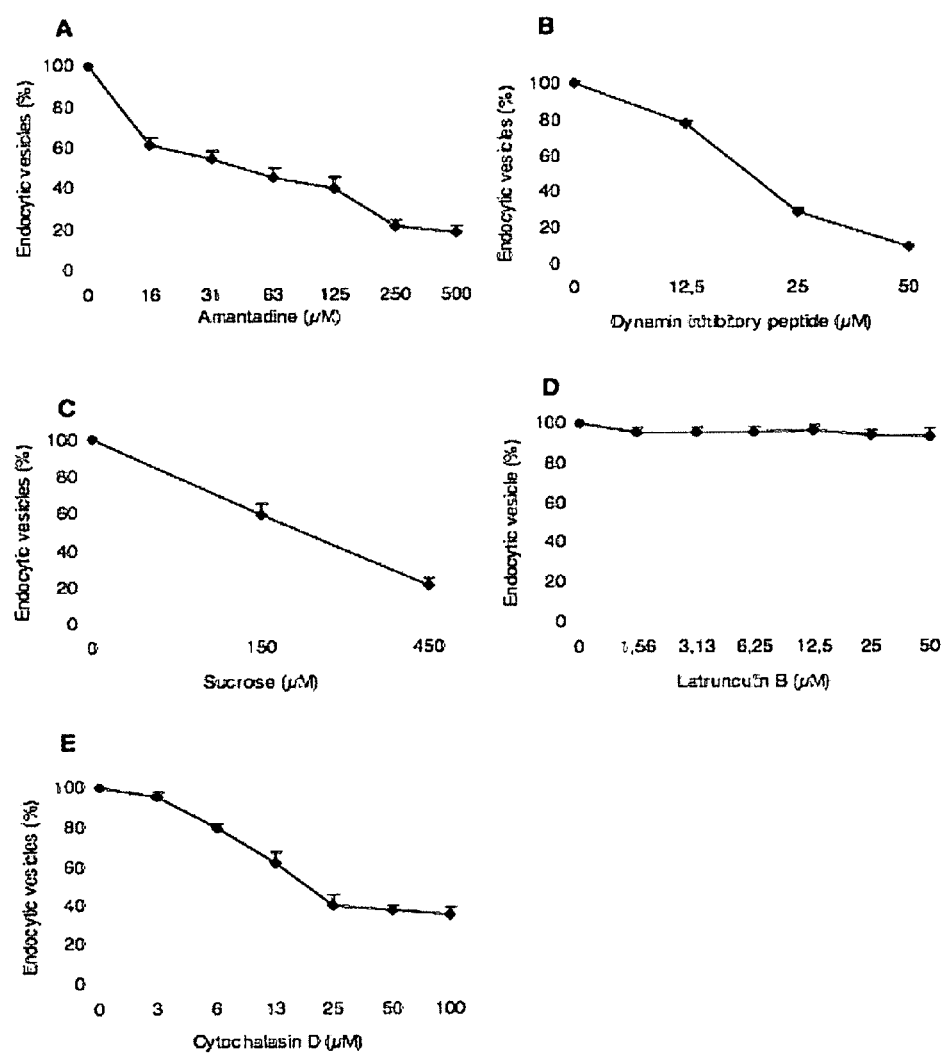
FIG. 4 Effect of different inhibitors on FLUOS-labeled-F4 internalization pAPN-BHK-21 cells. Cells were incubated with FLUOS-labeled-F4 in the presence of different concentrations of (A) amantadine, (B) dynamin inhibitory peptide and (C) sucrose which interfere with clathrin-mediated endocytosis, (D) latrunculin B which disrupts actin, and (E) cytochalasin D which inhibits G-actin polymerization to F-actin and budding of clathrin-coated vesicles. The number of internalized vesicles was quantified and expressed as a percentage relative to the number of internalized vesicles in the absence of the inhibitor. Data represent the mean±standard deviation of 3 independent experiments.

As shown in FIG. 4, hypertonic sucrose and the inhibitors amantadine, dynamin inhibitory peptide and cytochalasin D reduced the F4 internalization in pAPN-BHK cells in a concentration dependent manner, while latrunculin B had no effect. BHK cells were also tested, but showed no internalization.

Since our data indicate that F4 is internalized via clathrin-mediated endocytosis, double immunofluorescence staining for F4ac and clathrin were performed on pAPN-BHK cells to confirm the potential involvement of clathrin. A clear co-localization between F4ac and clathrin could be observed during F4 invagination from the plasma membrane.

Vesicles that were completely internalized in the cytoplasm no longer co-localized with clathrin, indicating that they released their clathrin coat. Together, these data show that F4ac internalization is clathrin-mediated.

Example 2

Expression of APN in Enterocytes of Pig, Mice, Sheep and Men

Methods
Preparation and Pre-Incubation of Pig Jejunum Loops

Three F4-seronegative pigs, (with SS or SR susceptible genotype in the DNA-based marker test for XbaI polymorfims in the mucin 4 gene (Jørgensen et al., 2004) were used in the present study. Five days postweaning, the pigs were laparotomized, under intramuscular anesthesia with tiletamine and zolazepam (Zoletil 100; Virbac S. A., Carros, France) supplemented with 2% xylazine (Xyl-M1; VMRD, Arendonk, Belgium) (0.22 ml/kg) after an overnight fast. In F4R+ pigs (Belgian Landrace_English Landrace), isolated loops of approximately 5 cm in length were prepared in the jejunum (small intestine) without Peyerse Plates (PP) (jejunal loops) (Moon et al., 1966). Care was taken to minimize surgical trauma and to maintain an adequate blood supply to the ligated segments. In mid-jejunum, 4 loops were created which were injected with buffer (5 ml PBS containing 1 mM CaCl2 and 1 mM MgCl2),
    F4 (3 mg in 5 ml buffer),
    FLUOS-labeled-F4 (3 mg in 5 ml buffer), or
    polyclonal antibody against APN.

The gut was returned to the abdominal cavity, the abdomen was closed and general anaesthesia was maintained. After 1 hour, the animals were euthanised by intravenous injection of an overdose of pentobarbital (24 mg/kg; Nembutal, Sanofi Sante' Animale, Brussels, Belgium).
Tissue Sampling for Immunohistochemical Analysis Immediately after euthanasia of the pigs, the loops were excised, opened at both ends and flushed with cold PBS containing 1 mM CaCl2 and 1 mM MgCl2. A cylinder of 2 cm in length was embedded in 2% (w/v) methocel. (Fluka, Bornem, Belgium) in water and frozen in liquid nitrogen. Cryosections from the frozen tissue samples, approximately 8-µm thick, were mounted on 3-aminopropyl-triethoxysilane (APES; Sigma-Aldrich) coated glass slides. After drying, the sections were fixed in acetone and stored at −70° C.

The F4R status of the pigs was confirmed using the in vitro villous adhesion assay (Van den Broeck et al., 1999). Adhesion of more than 5 bacteria per 250 µm villous brush border length was noted as positive.
Immunocytochemistry of an APN-Expressing Cell Line The BHK-21 and pAPN transfected BHK-21 cells (kindly gifted by Dr. Enjuanes and Dr. Laude) were cultured in DMEM with 5% FCS, 1% L-Glu, 1% P/S, 1% sodiumpyruvate (Gibco BRL, Life Technologies Inc., Paisley, Scotland), 1% non-essential amino acids (Gibco BRL, Life Technologies Inc., Paisley, Scotland). For selection of the transfected cells the medium was supplemented with 1.5 mg/ml geneticin G418 (Sigma-Aldrich Chemie GmbH, Steinheim, Germany). The BHK-21 and pAPN transfected BHK-21 cells were incubated at 37° C. with polyclonal anti-porcine APN rabbit antibodies to allow internalization or with rabbit serum without APN-specific antibodies to determine a specific binding and uptake. After 45 minutes, cells were washed with PBS$^+$ and fixed with 3% PFA, permeabilized with 0.1% Triton X-100 and stained with 1:500 goat anti-rabbit IgG(H+L chain) FITC-labeled antibodies in PBS$^+$ for 1 h at 37° C. Finally, cells were washed with PBS$^+$, mounted and analyzed by confocal microscopy.
Immunohistochemical Staining of Pig Jejunum Loops Cryosections of pig jejunum loops were air-dried during 1 h, washed in PBS for 5 min and incubated with 10% (v/v) goat or sheep serum in PBS for 30 min at 37° C.

The sections of the loop injected with buffer solution (control) and the sections of the loop injected with FLUOS-labeled F4 were sequentially incubated with the APN-specific antibodies diluted in PBS and the TexRed1-conjugated anti-rabbit or mouse antibody in PBS with 5% pig serum, both during 1 h at 37° C.
    Cryosections of loops incubated with the polyclonal anti-APN antiserum and as a control some sections of the PBS loop were incubated with the TexRed1-conjugated antibodies alone.
    To demonstrate uptake of F4 by APN some of the sections incubated with FLUOS-labeled F4 were stained with the anti-SWC3 monoclonal antibody (74-22-15)(Stokes et al., 1996).

The sections were mounted in glycerol containing 0.223 M 1,4-diazobicyclo-(2,2,2)-octane (DABCO; Sigma-Aldrich) to counter photobleaching. Whereafter they were looked at by immunofluorescence microscopy and confocal laser scanning microscopy.

For double staining of cryosections of loops will be incubated with F4, the sections will first be blocked during 30 min at 37° C. with 10% serum of the same species from which the first and the second secondary antibodies are derived. Subsequently, the following antibodies will sequentially be applied and incubated for 1 h at 37° C.:
    the first primary antibody,
    the first secondary antibody,
    the second primary antibody and
    the second secondary antibody.
    Cryosections will be looked at by immunofluorescence microscopy and confocal laser scanning microscopy as described above.

Immunohistochemical Staining of Sheep, Man and Mice Tissue

Cryosections of the small intestine of sheep, man and mice were tested for binding of the porcine APN-specific antibodies. Mouse tissue was also incubated with a mouse APN-specific antibody. Binding was demonstrated using a conjugate specific for the immunoglobulins of the species used to demonstrate APN and labeled with FITC.

Results

Immunocytochemistry of an APN-Expressing Cell Line

Figure 5:
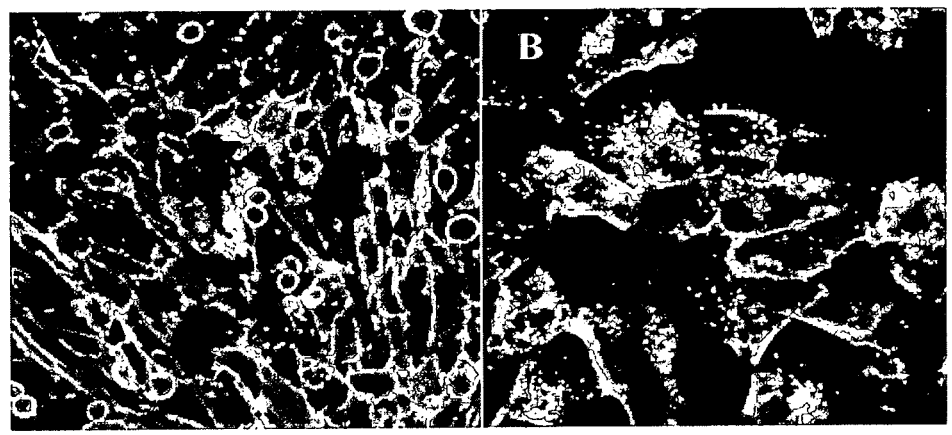
FIG. 5 APN expressing BHK cells were incubated with porcine APN specific antibodies. (A) represents the cells immediately after incubation, the intensely stained round circles represent detaching/dying cells (B) the cells 45 minutes after incubation. Anti-APN becomes endocytosed and can be seen in the vesicles in the cytoplasm of the BHK cells.

Staining of APN-expressing BHK cells incubated with the polyclonal anti-porcine APN antibodies demonstrated uptake of the antibodies, which can be found in the cytoplasm of the cells 45 minutes after incubation (FIG. 5B) BHK cells that did not express APN did not show this fluorescence in their cytoplasm.

Immunohistochemical Staining of Pig Jejunum Loops

Loops injected with PBS showed no specific-immunofluorescence in any of the performed stainings.

Loops injected with F4-FLUOS showed endocytosis of F4 by villus enterocytes. Furthermore, F4 could be demonstrated in the lamina propria beneath the epithelial layer and in some SWC3+ cells. Similar observations were done for loops injected with F4.

Figure 6:
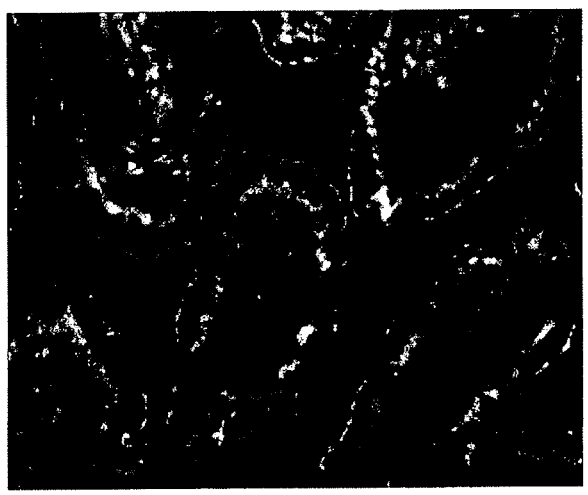
FIG. 6 Binding of PorcineAPN-specific antibodies to the brush border of human small intestinal enterocytes (arrow).

In loops injected with anti-APN antibodies, binding of APN could be demonstrated to the brush border of enterocytes. The same antibodies also bound to the brush border of human (FIG. 6) and sheep small intestinal enterocytes, but not to those of mice. However mouse APN could be demonstrated on enterocytes of mice with a mouse APN-specific monoclonal antibody.

Immunohistochemical Staining of Sheep, Men and Mice Tissue

Staining of cryosections of intestine of pig loops incubated with FLUOS-labeled F4 showed colocalization of F4 and APN using confocal laser scanning microscopy.

Discussion

Our results demonstrate the presence of APN on enterocytes of pigs with antibodies that cross react with human and sheep APN, but not with mouse APN. The latter is recognized by mouse APN-specific antibodies. APN-expressing BHK cells endocytose the antibodies.

Example 3

Binding of F4ab, F4ac and F4ad to Porcine APN

We demonstrated binding of F4ac fimbriae of enterotoxigenic *E. coli* to porcine APN from brush border enterocytes (Rasschaert, 2008). However, 3 serological variants of F4 fimbriae have been demonstrated: F4ab, F4ac and F4ad. Binding has been demonstrated to glycoproteins and glycolipids of different molecular weights as reviewed in Van den Broeck et al. (2000). When the three variants of F4 (F4ab, F4ac, and F4ad) are considered, six porcine phenotypes can be distinguished with regard to the brush border adhesiveness as represented in table 3: phenotype A binds all three variants, phenotype B binds F4ab and F4ac, phenotype C binds F4ab and F4ad, phenotype D binds F4ad, phenotype E binds none of the variants, and phenotype F binds F4ab. Therefore the aim of the present study was to determine binding of the 3 F4 variants to porcine APN, which we identified as one of the glycoproteins recognized by F4ac.

TABLE 3

Phenotypes with regard to binding of the 3 F4 variants to brush borders of pigs (reviewed in Van den Broeck et al., 2000)

| Fenotype | F4ab | F4ac | F4ad | Receptor | Identification of receptor |
|---|---|---|---|---|---|
| Type A | + | + | + | bc en bcd | glycoproteins 210 and 240 kDa en glycoproteins 45-70 kDa |

TABLE 3-continued

Phenotypes with regard to binding of the 3 F4 variants to brush borders of pigs (reviewed in Van den Broeck et al., 2000)

| Fenotype | F4ab | F4ac | F4ad | Receptor | Identification of receptor |
|---|---|---|---|---|---|
| Type B | + | + | − | bc | glycoproteins 210 and 240 kDa |
| Type C | + | − | + | d en b | |
| Type D | − | − | + | d | glycosphingolipid |
| Type E | − | − | − | | |
| Type F | + | − | − | b | glycoprotein 74 kDa |

Methods

In Vitro Villous Adhesion Assay for F4R Characterisation of the Pigs

Small intestinal villi of pigs were tested in order to determine the presence or absence of the F4R on brush borders of small intestinal villous enterocytes using an in vitro villous adhesion assay as described by Van den Broeck et al. (1999). Adhesion of more than 5 bacteria per 250 µm villous brush border length was noted as positive.

Enterocyte Preparations

Small intestinal epithelial cells from the pig were isolated by the method of Lundqvist et al., (1992). The small intestine (jejunum) was washed twice with Krebs-Henseleit buffer (0.12 M NaCl, 0.014 M KCl, 0.001 M KH2PO4 and 0.025 M NaHCO3 adjusted to pH 7.4). The segment was inverted and cut into small fragments. To remove the enterocytes from the tissue fragments, the fragments were incubated in Hanks' balanced salt solution (HBSS) with 1 mM dithiotreitol (DTT, Sigma-Aldrich Chemie GmbH, Steinheim, Germany) and 1.5 mM EDTA (Sigma-Aldrich Chemie GmbH, Steinheim, Germany) while shaking at 200 rpm for 30 min at 37° C. The obtained cell suspension was passed through organza to remove the mucus and centrifuged at 1,811×g for 10 min at 4° C. Enterocytes were washed 3 times in HBSS with 0.1 mM of the protease inhibitor, phenylmethylsulfonyl fluoride (PMSF, Sigma-Aldrich Chemie GmbH, Steinheim, Germany). The purity of the samples was analyzed by light microscopy on the basis of the normal morphology for enterocytes; our samples contained 85% enterocytes. Either brush border membrane vesicles were prepared, as described below, or the enterocyte suspension was used directly.

Membrane Preparations

Brush border membrane vesicles (BBMV) of the small intestine were prepared from the F4Rpos and F4Rneg pigs by the method of Kessler et al., (1978) with a slight modification. Enterocytes were washed twice in PBS with 0.1 mM PMSF and were resuspended in Tris-HCl buffer (2 mM, pH 7.2) containing 50 mM mannitol in ratio 3:1 (vol/vol) whereafter cells were homogenized for 2 min with an Ultra Turrax (Janke & Kunkel, I K A Labortechnik, Staufen, Germany). Subsequently, CaCl2 was added to the homogenate to a final concentration of 10 mM and placed on ice for 15 min. Then the homogenate was centrifuged at 27,000×g for 30 min and washed with Tris buffer (pH 7.5) containing 50 mM mannitol and 10 mM HEPES and centrifuged again. The pellet was resuspended in the same buffer and used for the study. The protein concentration of the obtained BBMV was determined using the bicinchoninic acid (BCA) reaction with bovine serum albumin (BSA) as standard (ICN Biomedicals, Belgium).

Binding of F4 to APN of Different Sources.

Binding of the different F4 variants to APN was tested in immunoblotting. Hereto brush border proteins or enterocyte proteins were solubilized in sample buffer containing β-mercaptoethanol and were heated to 95° C. for 10 min prior to electrophoresis. SDS-PAGE separated brush border proteins were blotted onto a PVDF membrane. The membrane was subsequently blocked with 5% non-fat dry milk/PBS/0.3% Tween-80 overnight at 4° C. and incubated for 1 hour at room temperature with 2 μg/ml F4. Thereafter, the membrane was incubated with the F4 specific MAb IMM01 (Van der Stede et al., 2002) for 1 hour. Subsequently, the membrane was incubated with rabbit anti-mouse horseradish peroxidase conjugate (DAKO, Glostrup, Denmark) for 1 hour (dilution 1:1000) and incubated with amino-ethyl carbazole (AEC). In between each step, the membrane was washed three times with PBS/0.3% Tween-20 for 5 minutes.

Results

The results are summarized in table 4. F4ab and F4ac show a similar binding capacity to the intestinal APN (enterocyte and BBMV), whereas binding of F4ad was weaker. F4ab and F4ad (although weaker) but not F4ac also bound to the kidney APN.

TABLE 4

Binding of 3 F4 variants to APN in immunoblotting

|  | F4ab | F4ac | F4ad |
| --- | --- | --- | --- |
| Enterocyte APN | ++ | ++ | + |
| BBMV* APN | ++ | ++ | ±** |
| Porcine kidney APN | ++ | − | + |

*BBMV = brush border membrane vesicles;
**Weak binding

Discussion

Our results suggest that F4ab and F4ac recognize APN similarly in enterocytes suggesting that F4ab can also be used to target intestinal APN.

Example 4

Oral Immunization of Mice by Targeting APN with APN-Specific Fab Fragments

F4ac fimbriae of enterotoxigenic *E. coli* are strong immunogens when given orally to pigs. We identified aminopeptidase N on brush borders of enterocytes as the receptor to which F4ac is adhering. In this experiment we want to demonstrate the potential of APN to be used as target for induction of an intestinal mucosal immune response.

Methods

Preparation of (Fab)2 Fragments

The (Fab)2 fragments were produced by pepsin digestion of a miceAPN-specific rat IgG2a monoclonal antibody, followed by removal of Fc fragments using protein G Montage Spin columns (Millipore). The (Fab)2 fragments were further reduced to monomeric Fab using β-mercaptoethanol.

Immunization of Mice

Balb/c mice (10 to 12 weeks old) were orally immunized with the Fab fragments at day 0, 1 and 3 followed by a booster-immunization at day 14. Each time dosages of 50 μg (low dose, 6 mice) or of 250 μg (high dose, 6 mice) of the antibody fragments in PBS was given. Six mice were given 50 μg of the (Fab)2 fragments (Fab2 group). A control group of 6 mice only received PBS.

Analysis of the Mice

Serum was collected at day 0, 14 (at the moment of the immunization) and at day 28 to determine the anti rat-IgG2a-specific antibody response. Mice were euthanized at day 28 and mesenteric lymph nodes and spleen were pooled per group to determine the number of anti-rat IgG2a IgM, IgG and IgA producing cells (ASC), by Elispot analysis.

Results

A clear anti-rat IgG2a specific antibody response is seen in the serum of the mice of the immunized groups at day 28 of the experiment which is not seen in the control group. The response is slightly higher in the high dose group than in the low dose group.

The Elispot assay demonstrated the presence of mainly IgA ASC in mesenteric lymph nodes of the orally immunized mice and of mainly IgG in the spleen of these mice and no ASC in the control group.

Discussion

Targetting APN, expressed on intestinal epithelial cells, via the oral route using APN specific Fab fragments, results in a systemic and mucosal immune response against these antibodies.

Example 5

Vaccination of Pigs Against *Toxoplasma gondii* Infections by Targeting GRA1-GRA7 Towards APN Using APN-Specific Antibody Fragments We demonstrated that targeting of APN using F4 fimbriae resulted in an F4-specific immune response. Furthermore by giving APN-specific Fab antibody fragments via the oral route to mice, a mucosal and systemic antibody response could be induced against the antibody fragments. The aim of the present study is to demonstrate that the antibody fragments can be used to target another antigen towards the mucosa with the aim to deliver this antigen towards the mucosal and systemic immune system for induction of a specific immune response.

Methods

*T. gondii* Strains

*T. gondii* strains RH and IPB-G are routinely maintained by mouse passage. RH is a zymodeme type I strain (Sabin, 1941) and is harvested from the peritoneal cavity of infected Swiss mice 4 days after intraperitoneal (IP) inoculation. IPB-G is a zymodeme II type strain (Vercammen et al., 1998) and is harvested from the brains of chronically infected Swiss mice. Total lysate antigen (TLA) will be prepared from RH tachyzoites as described previously (Vercammen et al., 2000)

*Toxoplasma* Immunogen

Recombinant rGRA1 and rGRA7 are purified as described previously [Jongert et al., 2007; Bivas-Benita et al., 2003]. Rabbit porcine APN-specific Fab antibody fragments will be prepared as described for mice with the difference that the IgG antibodies will be purified from serum over a protein A column and that protein A columns are also used for removing the Fc fragments after pepsin digestion. rGRA1 and rGRA7 will be chemically conjugated to the Fab fragments. Hereto the antibody and the antigen will be treated with SPDP (Reaction A) to create pyridyl-dithiol-activated proteins. Subsequently the pyridyldithiol-activated antigen will be treated with DTT to reduce the disulfide bond (Reaction B). After purification, the pyridyl-dithiol-activated monoclonal antibody and the sulfhydryl-activated antigen will be mixed to produce the coupling product (Reaction C). This protocol has already been successfully applied using the antigen human serum albumin.

Immunization and Infection of Pigs

Fourteen conventionally bred pigs (Belgian Landrace× Piëtrain), *Toxoplasma* seronegative as determined by indirect immunofluorescence, will be weaned at the age of 4 weeks and housed in isolation units. Seven pigs will be orally immunized with the *Toxoplasma* immunogen containing 500 µg rGRA1-IgGFab and 500 µg rGRA6-Fab. This dose is given 3 subsequent days and again 14 days after the first immunization. Seven control pigs will receive PBS. Twenty-four hours before each immunization the acidic gastric pH will be increased by addition of 20 mg rabeprazolum (Pariet, Janssen-Cilag, Berchem, Belgium) as described by Verdonck et al., 2004. All pigs will be orally infected with 3000 mice brain cysts of the Prugniaud strain 2 weeks after the booster-immunization. These cysts will be isolated from the brains of mice infected 2 months earlier with Prugniaud strain of *T. gondii* (Martrou et al. 1956). Brains will be homogenized and the cysts counted and diluted as required. Pigs will be euthanized 8 weeks post infection Evaluation of the Humoral Immune Response The antibody response will be analyzed by sampling serum at days −7, 0, 21, 28, 31, 35, 38, 42, and then weekly until day 84. The *T. gondii*-specific humoral immune response will be analyzed by ELISA for determination of the IgG titer against rGRA1, rGRA7 and TLA as described previously (Jongert et al., 2007), using an HRP conjugated anti-pig IgG (AbD Serotec), Oxford, UK). All sera will be used in twofold dilutions starting at a dilution of 1/50. Endpoint titers will be defined as the dilution where the optical density (OD450) exceeded the cutoff value. The cut-off value will be calculated from preimmune sera (day-7) at a 1/50 dilution, with cut-off value=mean OD450+3×SD OD450.

Evaluation of the Cellular Immune Response

On days 26, 42, 56 and 70, peripheral blood monomorphonuclear cells (PBMCs) will be isolated as described by Van den Broeck et al. (1999) and restimulated with 10 µg/ml rGRA1, 10 µg/ml rGRA7 or medium, according to a previously described protocol (Melkebeek et al., 2007). Proliferation will be determined by an 18 h H3+-thymidine incorporation on day 3 of the proliferation assay. After euthanasia of the pigs, monomorphonuclear cells will be isolated from the spleen as described by Van der Stede et al. (2002) and cultured as described by Melkebeek et al. (2007). Cells will be restimulated with 10 µg of rGRA1, rGRA7 or medium for 18 h, whereafter porcine IFN-gamma will be determined in the medium using a commercial ELISA.

Evaluation of the Intestinal Mucosal Immune Response and Response in Spleen

The GRA1 and GRA7-specific IgA antibody secreting cells (ASC) in the lamina propria, jejunal Peyer's patches and mesenteric lymph nodes and the GRA1 and GRA7-specific IgG ASC in spleen will be analyzed by ELIspot in 2 pigs of each group at the moment of the challenge infection and for the rest of the pigs 56 days post infection. Briefly, maxisorb 96-well plates will be coated with 2 µg/ml rGRA1 or rGRA7 in PBS. Thereafter, monomorphonuclear cell suspensions (MC) at a concentration of $10^7$ cells/ml in leukocyte medium will be added to the plates (100 µl/well). Then the plates will be incubated for 10 h at 37° C. in a humidified CO2 atmosphere. Several washes with PBS+ 0.2% Tween® 20 will be performed to remove the cells from the plates. Subsequently, optimally diluted mouse anti-swine IgA monoclonal antibodies (mAbs) or anti-swine IgG mAbs will be added to the wells followed by anti-mouse-biotine and streptavidine-HRP. Each incubation step will last 1 h at 37° C. and will be followed by three washes with PBS+0.2% Tween® 20. Detection will be performed as described by Van den Broeck et al., 1999. The amount of ASCs per $5 \times 10^6$ MC will be obtained by counting the spots in 5 wells ($10^6$ MC/well).

Furthermore, MC will be restimulated with rGRA1 or rGRA7, as described in the paragraph on the cellular immune response, to determine lymphocyte proliferation and IFN-gamma production. MC cells of lamina propria, Peyer's patches, mesenteric lymph nodes and spleen will be prepared as described (Verdonck et al., 2002).

Protection Against Infection.

Protection against infection will be determined 8 weeks after challenge infection by examining brain, heart, m. Gastrocnemius and m. Psoas major using a mouse bioassay and qPCR. Both techniques will be performed in the laboratory of Toxoplasmosis (WIV, Brussels). If at this moment less or no parasites are found in the tissues of the immunized pigs in comparison with the control group, this indicates that there is an improved immune response.

The invention claimed is:

1. A method of delivering a heterologous antigen or therapeutic molecule across the intestinal mucosal barrier of a subject, said method comprising:
    orally administering to said subject a chimeric molecule comprising (a) an antibody, or fragment thereof, that specifically binds the aminopeptidase N (APN) receptor on mucosal intestinal epithelial cells, conjugated to
    (b) a heterologous antigen or therapeutic molecule,
    wherein said heterologous antigen or therapeutic molecule is delivered across the intestinal mucosal barrier by clathrin-mediated transcytosis.

2. The method according to claim 1, wherein said antigen or therapeutic molecule induces or modulates a mucosal immune response.

3. The method according to claim 1, wherein the method results in the treatment of an infection of the gastrointestinal tract.

4. The method according to claim 1, wherein the mucosal epithelial cells are enterocytes.

5. The method according to claim 1, wherein the chimeric molecule is part of a pharmaceutical composition further comprising a pharmaceutically acceptable carrier or diluent.

6. The method according to claim 1, wherein the antibody or fragment is coupled with a particle selected from the group consisting of microspheres, microparticles, nanoparticles, nanospheres, and liposomes, wherein said particle is loaded with said heterologous antigen or therapeutic molecule.

7. The method according to claim 1, wherein the antibody is chemically conjugated to said antigen or therapeutic molecule.

8. The method according to claim 1, wherein said heterologous antigen or therapeutic molecule is selected from the group consisting of proteins, lipids, nucleic acids, glycolipids, glycoproteins, carbohydrates, oligosaccharides and polysaccharides.

9. The method according to claim 1, wherein said heterologous antigen is a parasitic, viral, bacterial, mycotic or yeast derived antigen.

10. The method according to claim 1, wherein said chimeric molecule comprises from about 5 to 95% by weight of said anti-APN antibody, or fragment thereof, and from about 1 to 95% by weight of a heterologous antigen or therapeutic molecule.

\* \* \* \* \*

UNITED STATES PATENT AND TRADEMARK OFFICE
CERTIFICATE OF CORRECTION

| | |
|---|---|
| PATENT NO. | : 9,636,417 B2 |
| APPLICATION NO. | : 14/597269 |
| DATED | : May 2, 2017 |
| INVENTOR(S) | : Kristien Rasschaert et al. |

It is certified that error appears in the above-identified patent and that said Letters Patent is hereby corrected as shown below:

On the Title Page

(57) ABSTRACT:
"The invention is based on the identification of aminopeptidase N (APN) as the receptor for F4 fimbriae of enterotoxigenic E. coli (ETEC). Based on the observation that oral administration of F4 fimbriae induces a protective intestinal mucosal immune response against a subsequent challenge with F4 ETEC, and the observation that the internalization of said F4fimbriae is clathrin-mediated, the present invention provides the characterization of APN as a target useful in: in an in vitro assay to screen for molecules that are capable to mimic the clathrin-mediated F4 endocytosis; in an in vitro assay to screen for molecules that are capable to modulate the binding of F4 fimbriae with APN; in the development of a carrier for the delivery of antigens / therapeutics, i.e. immunomodulators to the intestinal submucosa or the intestinal mucosa-associated lymphoid tissue, wherein said carrier comprises an APN specific target molecule that mimics the clathrin-mediated F4 endocytosis. The use of the carriers thus identified or the treatments thus identified, in a method of inducing an antigen specific intestinal mucosal immune response, and/or in the treatment of bacterial diarrhea, is a further aspect of the present invention."

Should read:

(57) ABSTRACT
--The invention is based on the identification of aminopeptidase N (APN) as the receptor for F4 fimbriae of enterotoxigenic E. coli (ETEC). Based on the observation that oral administration of F4 fimbriae induces a protective intestinal mucosal immune response against a subsequent challenge with F4 ETEC, and the observation that the internalization of said F4 fimbriae is clathrin-mediated, the present invention provides the characterization of APN as a target useful in: in an in vitro assay to screen for molecules that are capable to mimic the clathrin-mediated F4 endocytosis; in an in vitro assay to screen for molecules that are capable to modulate the binding of F4 fimbriae with APN; in the development of a carrier for the delivery of antigens / therapeutics, i.e. immunomodulators to the intestinal submucosa or the intestinal mucosa-associated lymphoid tissue, wherein said carrier comprises an APN specific target molecule that mimics the clathrin-mediated F4 endocytosis. The use of the carriers thus identified or the treatments thus identified, in a method of inducing an antigen Signed and Sealed this
Twenty-seventh Day of February, 2018

Andrei Iancu
*Director of the United States Patent and Trademark Office* specific intestinal mucosal immune response, and/or in the treatment of bacterial diarrhea, is a further aspect of the present invention.--;

In the Specification

Column 4, Line 35:
"immune response include all kind of infections of the"
Should read:
--immune response include all kinds of infections of the--;

Column 4, Lines 38-40:
"matory and Irratable Bowel disease and IgA deficiencies. In particular said condition consists of diarrhoea, more in particular bacterial diarrhoea."
Should read:
--matory and Irritable Bowel disease and IgA deficiencies. In particular said condition consists of diarrhea, more in particular bacterial diarrhea.--;

Column 5, Line 33:
"mucosal immune response e.g. an anti-diarrhoea compound"
Should read:
--mucosal immune response e.g. an anti-diarrhea compound--;

Column 6, Line 4:
"FIG. 6 Binding of PorcineAPN-specific antibodies to the"
Should read:
--FIG. 6 Binding of Porcine APN-specific antibodies to the--;

Column 6, Line 58:
""aminopeptidase N (APN)" is a type II membrane gly-"
Should read:
--"Aminopeptidase N (APN)" is a type II membrane gly- --;

Column 6, Lines 62-63:
"membranes. cDNA sequences that encodes a porcine APN (pAPN) polypeptide (SwiwwProt accession number P15145), a murine APN polypeptide (SwissProt access number P15684) a feline APN polypeptide (SwissProt access number P79171) a donkey APN polypeptide (Genbank access number"
Should read:
--membranes. cDNA sequences that encodes a porcine APN (pAPN) polypeptide (SwissProt accession number P15145), a murine APN polypeptide (SwissProt access number P15684) a feline APN polypeptide (SwissProt access number P79171) a donkey APN polypeptide (Genbank access number--;

Column 7, Line 38:
"molecule encoding for porcine APN (Genbank Acession No"

Should read:
--molecule encoding for porcine APN (Genbank Accession No--;

Column 14, Line 40:
"example described in Advanced drug Delivery Reviews,"
Should read:
--example described in Advanced Drug Delivery Reviews,--;

Column 15, Lines 30-32:
"matory and Irratable Bowel disease and IgA deficiencies. In particular said condition consists of diarrhoea, more in particular bacterial diarrhoea."
Should read:
--matory and Irritable Bowel disease and IgA deficiencies. In particular said condition consists of diarrhea, more in particular bacterial diarrhea.--;

Column 15, Line 38:
"receptor, more in particular through the through the"
Should read:
--receptor, more in particular through the--;

Column 15, Line 52:
"Such conditions may include all kind of infections of the"
Should read:
--Such conditions may include all kinds of infections of the--;

Column 15, Lines 55-57:
"matory and Irratable Bowel disease and IgA deficiencies. In particular said condition consists of diarrhoea, more in particular bacterial diarrhoea."
Should read:
--matory and Irritable Bowel disease and IgA deficiencies. In particular said condition consists of diarrhea, more in particular bacterial diarrhea.--;

Column 16, Line 31:
"selected from the group consisting of gleatin agar, starch,"
Should read:
--selected from the group consisting of gelatin agar, starch,--;

Column 16, Lines 33-34:
"lactic aced, glycolide-L(-) lactide poly(episilon-caprolactone, poly(epsilon-caprolactone-CO-lactic acid), poly(epsi-"
Should read:
--lactic acid, glycolide-L(-) lactide poly(episilon-caprolactone), poly(epsilon-caprolactone-CO-lactic acid), poly(epsi- --;

Column 16, Line 42:
"colic acid, polylactic aced, glycolide-L(-) lactide poly"

Should read:
--colic acid, polylactic acid, glycolide-L(-) lactide poly--;

Column 17, Line 63:
"parental compositions is highly dependent on the specific"
Should read:
--parenteral compositions is highly dependent on the specific--;

Column 20, Lines 26-27:
"ramping), 250 V for 30 min (lineair ramping), 1000 V for 30 min (lineair ramping), rapid ramping to 8000 V in 2h and"
Should read:
--ramping), 250 V for 30 min (linear ramping), 1000 V for 30 min (linear ramping), rapid ramping to 8000 V in 2h and--;

Table 2
Columns 25 and 26:
"Spotnr = these numbers refer to Figure 1;
the peptide score = the ion score for the individual peptide;
the protein score = probability Mowse score reported by matrix science where p<0.05 of the individual ions scores indicates identity or extensive homology;
Expect = the expectation value for the peptide match (the lower this value, the more significant the result);
Peptide = the sequence of the petide;
MWth = molecular weight of the protein spot obtained theoretically from the Swiss-Prot database (http://www.expasy.org);
pIth = isoelectric point of the protein spot obtained theoretically from the Swiss-Prot database (http://www.expas,org)"
Should read:
--Spotnr = these numbers refer to Figure 1;
the peptide score = the ion score for the individual peptide;
the protein score = probability Mowse score reported by matrix science where p<0.05 of the individual ions scores indicates identity or extensive homology;
Expect = the expectation value for the peptide match (the lower this value, the more significant the result);
Peptide = the sequence of the petide;
MWth = molecular weight of the protein spot obtained theoretically from the Swiss-Prot database (http://www.expasy.org);
pIth = isoelectric point of the protein spot obtained theoretically from the Swiss-Prot database (http://www.expas.org)--; and Column 33, Line 5:
"Piëtrain), Toxoplasma seronegative as determined by indi-"
Should read:
--Piétrain), Toxoplasma seronegative as determined by indi- --.